(12) United States Patent
Kaneko et al.

(10) Patent No.: US 11,970,662 B2
(45) Date of Patent: Apr. 30, 2024

(54) ELECTROCHROMIC ELEMENT

(71) Applicant: Ricoh Company, Ltd., Tokyo (JP)

(72) Inventors: Fuminari Kaneko, Kanagawa (JP); Daisuke Goto, Kanagawa (JP); Masato Shinoda, Kanagawa (JP); Ryo Kawamura, Kanagawa (JP); Naru Tanaka, Chiba (JP); Tohru Yashiro, Kanagawa (JP); Mamiko Inoue, Kanagawa (JP); Naoki Ura, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 793 days.

(21) Appl. No.: 16/941,732

(22) Filed: Jul. 29, 2020

(65) Prior Publication Data

US 2021/0032531 A1 Feb. 4, 2021

(30) Foreign Application Priority Data

Jul. 31, 2019 (JP) .................................. 2019-140655
Jul. 2, 2020 (JP) .................................. 2020-114998

(51) Int. Cl.
*C09K 9/02* (2006.01)
*C07C 313/06* (2006.01)
(Continued)

(52) U.S. Cl.
CPC .............. *C09K 9/02* (2013.01); *C07C 313/06* (2013.01); *C07F 9/58* (2013.01); *G02F 1/15165* (2019.01);
(Continued)

(58) Field of Classification Search
CPC .............. C09K 9/02; C09K 2211/1007; C09K 2211/1018; C07F 9/58; G02F 1/15165; C07C 313/06
See application file for complete search history.

(56) References Cited

U.S. PATENT DOCUMENTS

| 6,043,355 A | 3/2000 | Yashiro et al. |
| 6,600,589 B1 | 7/2003 | Berneth et al. |
| (Continued) | | |

FOREIGN PATENT DOCUMENTS

| EP | 3 268 448 A1 | 1/2018 |
| EP | 3 384 346 A1 | 10/2018 |
| (Continued) | | |

OTHER PUBLICATIONS

Extended European Search Report issued Jan. 12, 2021 in corresponding European Patent Application No. 20188455.8, 10 pages.
(Continued)

*Primary Examiner* — Bijan Ahvazi
(74) *Attorney, Agent, or Firm* — XSENSUS LLP

(57) ABSTRACT

An electrochromic element including: a first electrode; a second electrode disposed to face the first electrode with a gap between the first electrode and the second electrode; a first electrochromic layer disposed on or above the first electrode, including conductor or semiconductor nano-structures and an electrochromic compound; and an electrolyte layer including an electrolyte, disposed between the first electrochromic layer and the second electrode, wherein the electrochromic compound is a compound represented by General Formula 1, and an anion of the electrolyte is a monovalent anion having oxidation potential higher than reduction potential of a dication of General Formula 1 by 3.1 V or greater,

[General Formula 1]

(Continued)

where $X^-$ is a monovalent anion having oxidation potential higher than reduction potential of the dication of General Formula 1 by 3.1 V or greater and $W^{2+}$ is the dication represented by General Formula 2,

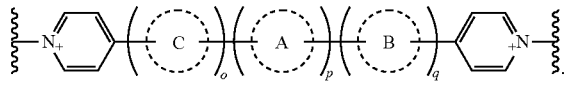

12 Claims, 1 Drawing Sheet

(51) Int. Cl.
  *C07F 9/58* (2006.01)
  *G02F 1/1516* (2019.01)
(52) U.S. Cl.
  CPC ............... *C09K 2211/1007* (2013.01); *C09K 2211/1018* (2013.01)

(56) References Cited

U.S. PATENT DOCUMENTS

| 9,688,706 | B2 | 6/2017 | Inoue et al. |
| 9,932,522 | B2 | 4/2018 | Goto et al. |
| 10,093,693 | B2 | 10/2018 | Sagisaka et al. |
| 10,634,970 | B2* | 4/2020 | Goto ..................... G02F 1/15 |
| 2008/0266642 | A1 | 10/2008 | Burrell et al. |
| 2009/0103162 | A1 | 4/2009 | Burrell et al. |
| 2015/0353819 | A1 | 12/2015 | Vasiliev et al. |
| 2016/0221949 | A1 | 8/2016 | Aiken et al. |
| 2016/0229803 | A1 | 8/2016 | Lin et al. |
| 2017/0235203 | A1 | 8/2017 | Yamamoto et al. |
| 2018/0044581 | A1 | 2/2018 | Sagisaka et al. |
| 2018/0155321 | A1* | 6/2018 | Kim ..................... C07D 401/14 |
| 2018/0314125 | A1 | 11/2018 | Goto et al. |
| 2019/0031694 | A1 | 1/2019 | Sagisaka et al. |
| 2019/0294015 | A1 | 9/2019 | Ura et al. |

FOREIGN PATENT DOCUMENTS

| JP | 2002-524762 | | 8/2002 |
| JP | 2006-518408 | A | 8/2006 |
| JP | 2008-052172 | | 3/2008 |
| JP | 2017-021327 | A | 1/2017 |
| JP | 2017-107153 | | 6/2017 |
| JP | 2017-206499 | | 11/2017 |
| JP | 2018-508034 | | 3/2018 |
| JP | 6456964 | | 12/2018 |
| WO | WO 2016/147543 A1 | | 9/2016 |
| WO | WO 2017/094218 A1 | | 6/2017 |

OTHER PUBLICATIONS

Michael Felderhoff et al, "Molecular Suppression of the Pimerization of Viologens (=4,4'-Bipyridinium Derivatives) Attached to Nanocrystalline Titanium Dioxide Thin-Film Electrodes", Helvetica Chimica Acta, Verlag Helvetica Chimica Acta, vol. 83, No. 1, Jan. 24, 2000, pp. 181-192, XP002554940, ISSN 0018-019X.
Office Action issued Jan. 23, 2024 in Japanese Patent Application No. 2020-114998, 6 pages.

* cited by examiner

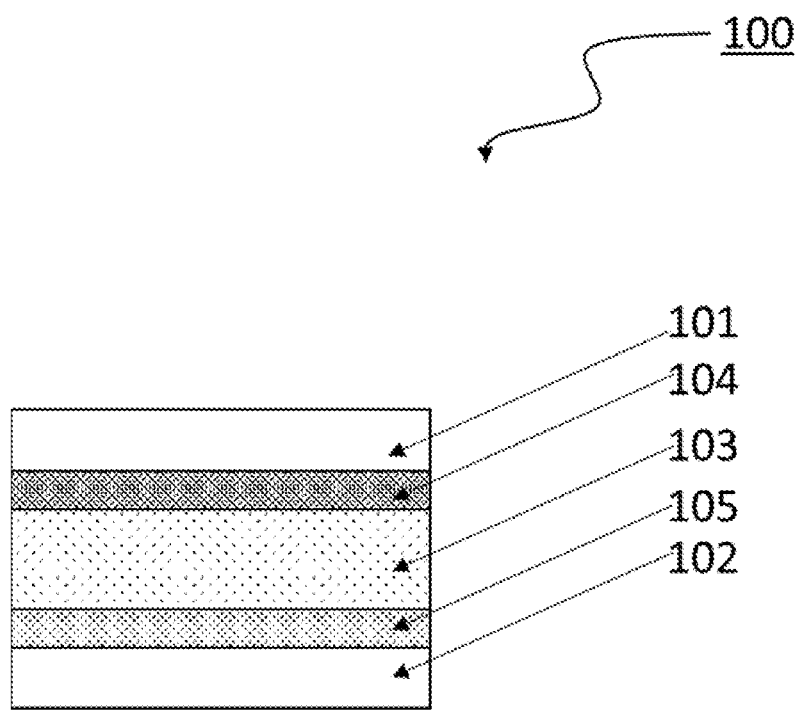

ELECTROCHROMIC ELEMENT

CROSS-REFERENCE TO RELATED APPLICATIONS

The present application claims priority under 35 U.S.C. § 119 to Japanese Patent Application No. 2019-140655 filed Jul. 31, 2019, and Japanese Patent Application No. 2020-114998 filed Jul. 2, 2020. The contents of which are incorporated herein by reference in their entirety.

BACKGROUND OF THE INVENTION

Field of the Invention

The present disclosure relates to an electrochromic element.

Description of the Related Art

Electrochromism is a phenomenon where a redox reaction is performed reversibly to reversibly change a color. The electrochromism is typically realized by a redox reaction occurred in a structure where an ion-conducting electrolyte layer is formed between a pair of electrodes facing to each other and the space between the electrodes is filled with the electrolyte layer.

When a transparent display element is produced using such an electrochromic element, or when an element having a structure where three coloring layers of cyan (C), magenta (M), and yellow (Y) is produced using the electrochromic element, it is important that the element is constructed using a reduction-type electrochromic material whose neutral state is a transparent state, or an oxidation-type electrochromic material whose neutral state is a transparent state. For such a display element exhibiting vivid colors, organic electrochromic materials that can be colored in various colors owing to substituents are suitably used.

As the electrochromic material, a viologen derivative exhibiting an electrochromic phenomenon has been used, where a neutral state of the viologen derivative is a colorless transparent and coloring of the viologen derivative occurs in a reduced state, etc. When the viologen derivative is used for a coloring layer of an element, titanium oxide is preferably used. It has been reported that high optical density or a high contrast ratio can be realized because a layer having an extremely high concentration of a viologen derivative can be formed by using titanium oxide particles are used as bearing particles of the electrochromic compound in a laminate structure. Moreover, excellent response and memory effects can be obtained by forming a solid layer of a viologen derivative, and a resultant element has an advantageous over an electrochromic element including a layer using a liquid or gel obtained by dissolving a viologen derivative in a solvent.

As such an electrochromic element, for example, disclosed is an electrochromic element using an electrochromic layer, in which a viologen derivative is deposited on conductor or semiconductor nano-structures (see, for example, Japanese Unexamined Patent Application Publication No. 2017-107153). As examples of a counter ion of the viologen derivative in the disclosed element, a Br ion (Br$^-$), a Cl ion (Cl$^-$), an I ion (I$^-$), an OTf (triflate) ion (OTf$^-$), a ClO$_4$ ion (ClO$_4^-$), a PF$_6$ ion (PF$_6^-$), and a BF$_4$ ion (BF$_4^-$) are listed.

As another example, moreover, an electrochromic element is also disclosed in Japanese Unexamined Patent Application Publication No. 2008-052172. As examples of a counter anion of a viologen derivative in the disclosed element, a Br ion (Br$^-$), a Cl ion (Cl$^-$), a ClO$_4$ ion (ClO$_4^-$), a PF$_6$ ion (PF$_6^-$), a BF$_4$ ion (BF$_4^-$), a TFSI ion (C$_2$F$_6$NO$_4$S$_2^-$), and FSI ion (CF$_3$SO$_3^-$) are listed.

The disclosed counter anions are not particularly limited, and as specific examples, only Br$^-$ and Cl$^-$ are disclosed. In addition, the above-mentioned literatures do not disclose at all how various properties of an element change depending on types of counter anions for use.

Meanwhile, various elements each using a solution or gel in which a viologen derivative is dissolved in a solution are disclosed. For example, Japanese Translation of PCT International Application Publication No. 2018-508034 discloses an element formed by dissolving a viologen derivative in a solvent to form a gel, followed by laminating the gel. Moreover, Japanese Unexamined Patent Application Publication No. 2017-206499 discloses a structure where a solution of a viologen derivative is sandwiched with electrodes. As a viologen derivative used in a solution system, moreover, for example, an aryl viologen derivative is disclosed in Japanese Patent No. 6456964. Several specific examples of an anion of a viologen derivative in the disclosed elements or materials are listed, but the anion for use is not necessarily limited. Particularly, the above-mentioned literatures do not mention a difference in properties depending on a type of an anion for use. Although several specific anions are listed, as described, for example, in Japanese Translation of PCT international Application Publication No. 2002-524762, an anion for use is selected merely by a reason whether the anion is inert to a redox reaction in a device or not.

SUMMARY OF THE INVENTION

According to an aspect of the present disclosure, an electrochromic element includes a first electrode, a second electrode disposed to face the first electrode with a gap between the first electrode and the second electrode, a first electrochromic layer disposed on or above the first electrode, where the first electrochromic layer includes conductor or semiconductor nano-structures and an electrochromic compound, and an electrolyte layer including an electrolyte, disposed between the first electrochromic layer and the second electrode. The electrochromic compound is a compound represented by General Formula 1, and an anion of the electrolyte is a monovalent anion having an oxidaization potential higher than a reduction potential of a dication of General Formula 1 by 3.1 V or greater.

[General Formula 1]

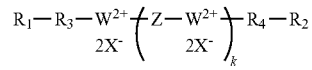

In General Formula 1, R$_1$ and R$_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, or a functional group that can bond to a hydroxyl group; and R$_3$ and R$_4$ are each an alkylene group having from 1 through 10 carbon atoms or an arylene group that may have a substituent and has 12 or less carbon atoms.

In General Formula 1, Z is alkylene, cycloalkylene, or a divalent group represented by —R$_7$—Y—R$_8$— (where R$_7$ and R$_8$ are each independently a single bond, alkylene, or cycloalkylene, and Y is arylene, cycloalkylene, heteroarylene, arylene-arylene, or arylene-CR'R"-arylene, with the proviso that R' and R" form a carbon ring group together with a carbon atom to which R' and R" are bonded). The alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl. "k" is 0 or 1.

In General Formula 1, X⁻ is a monovalent anion having an oxidation potential higher than a reduction potential of the dication of General Formula 1 by 3.1 V or greater.

In General Formula 1, W²⁺ is a dication represented by General Formula 2 below.

[General Formula 2]

In General Formula 2, o, p, and q are each independently 0 or 1; and A, B, and C are each independently an arylene group that may have a substituent and has from 2 through 20 carbon atoms, or a heterocycle group.

According to another aspect of the present disclosure, an electrochromic element includes a first electrode, a second electrode disposed to face the first electrode with a gap between the first electrode and the second electrode, a first electrochromic layer in which an electrochromic compound is deposited on conductor or semiconductor nano-structures, where the first electrochromic layer is disposed on or above the first electrode, and an electrolyte layer disposed between the first electrochromic layer and the second electrode. The electrochromic compound is a compound represented by General Formula 1.

[General Formula 1]

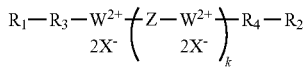

In General Formula 1, $R_1$ and $R_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, or a functional group that can bond to a hydroxyl group; and $R_3$ and $R_4$ are each an alkylene group having from 1 through 10 carbon atoms, or an arylene group that may have a substituent and has 12 or less carbon atoms.

In General Formula 1, Z is alkylene, cycloalkylene, or a divalent group represented by —$R_7$—Y—$R_8$ (where $R_7$ and $R_8$ are each independently a single bond, alkylene, or cycloalkylene, and Y is arylene, cycloalkylene, heteroarylene, arylene-arylene, or arylene-CR'R"-arylene, with the proviso that R' and R" form a carbon ring group together with a carbon atom to which R' and R" are bonded). The alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl. "k" is 0 or 1.

In General Formula 1, X⁻ is a monovalent anion having an oxidation potential higher than a reduction potential of the dication of General Formula 1 by 3.1 V or greater.

In General Formula 1, W²⁺ is a dication represented by General Formula 2 below.

[General Formula 2]

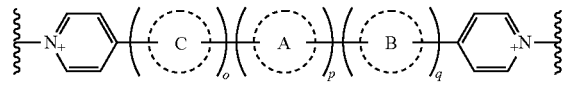

In General Formula 2, o, p, and q are each independently 0 or 1; and A, B, and C are each independently an arylene group that may have a substituent and has from 2 through 20 carbon atoms, or a heterocycle group.

BRIEF DESCRIPTION OF THE DRAWING

FIG. 1 is a schematic view illustrating a structural example of an electrochromic element of the present disclosure.

DESCRIPTION OF THE EMBODIMENTS

One reason why a viologen derivative can be used in a solution system without being particularly affected by a type of an anion of the viologen derivative is that a viologen derivative is not actually present as a complex or an ionic couple in a solution system, but the viologen derivative is dissolved in a solvent to cause ionic dissociation and is present as solvated free cations. Therefore, the viologen derivative exhibits the same behaviors as the viologen derivative cation regardless of a type of the original counter ion. Even if the viologen derivative is affected by free anions present relatively nearby, a significantly larger amount of an electrolyte than the amount of the viologen derivative is typically added to the solution system, influence of anions of the electrolyte is dominant, and therefore the viologen derivative is hardly affected by a type of the original counter ion.

On the other hand, properties of the viologen derivative are largely influenced by a type of a counter anion in an environment where the viologen derivative is present as an ionic couple or a complex, hardly any solvent or ions are present between molecules of the viologen derivative, or the viologen derivative is present at an extremely high concentration. The above-mentioned environment is a state where the viologen derivative is in a solid state, or is born on a carrier. Specifically, one of typical examples thereof is an electrochromic element using an electrochromic layer, in which the viologen derivative is deposited on conductor or semiconductor nano-structures. Therefore, the present inventors have found that a large change in properties of an electrochromic element depending on a counter anion of the viologen derivative is a unique problem associated with an electrochromic element using an electrochromic layer including the viologen derivative and conductor or semiconductor nano-structures.

As described above, it is the current situation that influence of a type of a counter anion on such an electrochromic element has not been sufficiently studied.

Therefore, the present inventors have diligently researched on a type of a counter anion for a dicatioin of an electrochromic element that has an electrochromic layer including a specific dication (a compound represented by General Formula 1), such as a viologen derivative, and conductor or semiconductor nano-structures. As a result, the present inventors have found that transparency of an electrochromic element in a bleached state changes depending on a type of a counter anion for use.

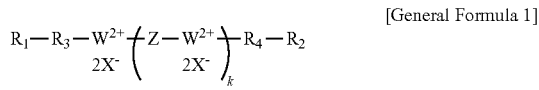
[General Formula 1]

In General Formula 1, $R_1$ and $R_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, or a functional group that can bond to a hydroxyl group; and $R_3$ and $R_4$ are each an alkylene group having from 1 through 10 carbon atoms or an arylene group that may have a substituent and has 12 or less carbon atoms.

In General Formula 1, Z is alkylene, cycloalkylene, or a divalent group represented by —$R_7$—Y—$R_8$ (where $R_7$ and $R_8$ are each independently a single bond, alkylene, or cycloalkylene, and Y is arylene, cycloalkylene, heteroarylene, arylene-arylene, or arylene-CR'R"-arylene, where R' and R" form a carbon ring group together with a carbon atom to which R' and R" are bonded), where the alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl. "k" is 0 or 1.

In General Formula 1, $X^-$ is an ion neutralizing the charge.

In General Formula 1, $W^{2+}$ is a dication represented by General Formula 2.

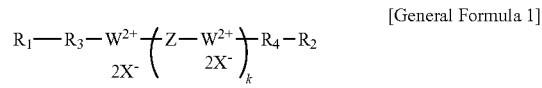
[General Formula 2]

In General Formula 2, o, p, and q are each independently 0 or 1; and A, B, and C are each independently an arylene group that may have a substituent and has from 2 through 20 carbon atoms, or a heterocycle group.

After conducting further researches, the present inventors have found the following insights. That is, high transparency in a bleached state can be achieved by using, as an anion for the specific dication, a monovalent anion having oxidation potential higher than reduction potential of the dication in General Formula 1 by 3.1 V or greater. The present disclosure has been accomplished based on the above-described insights.

In the present specification, having high transparency in a bleached state means that the first electrochromic layer has a low yellow index (YI) value. Specifically, high transparency is achieved in a bleached state as long as the YI value of the first electrochromic layer is kept low even through the YI value of the device itself may be high due to a color of the electrode.

The present disclosure has an object to provide an electrochromic element having high transparency in a bleached state.

The present disclosure can provide an electrochromic element having high transparency in a bleached state.

Embodiments for carrying out the present disclosure will be specifically described with reference to the drawing hereinafter.

(Electrochromic Element)

A structural example of the electrochromic element of the present disclosure is illustrated in FIG. 1. The electrochromic element includes a first electrode 101, a second electrode 102, an electrolyte layer 103, a first electrochromic layer 104, and a second electrochromic layer 105.

For example, an electrochromic element of the present disclosure include the following first embodiment and second embodiment.

First Embodiment

A first embodiment of the electrochromic element of the present disclosure includes a first electrode, a first electrode, a second electrode disposed to face the first electrode with a gap between the first electrode and the second electrode, a first electrochromic layer in which an electrochromic compound is deposited on conductor or semiconductor nano-structures, where the first electrochromic layer is disposed on or above the first electrode, and an electrolyte layer disposed between the first electrochromic layer and the second electrode. The electrochromic compound is a compound represented by General Formula 1.

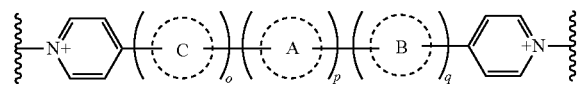
[General Formula 1]

In General Formula 1, $R_1$ and $R_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, or a functional group that can bond to a hydroxyl group; and $R_3$ and $R_4$ are each an alkylene group having from 1 through 10 carbon atoms or an arylene group that may have a substituent and has 12 or less carbon atoms.

In General Formula 1, Z is alkylene, cycloalkylene, or a divalent group represented by —$R_7$—Y—$R_8$ (where $R_7$ and $R_8$ are each independently a single bond, alkylene, or cycloalkylene, and Y is arylene, cycloalkylene, heteroarylene, arylene-arylene, or arylene-CR'R"-arylene, where R' and R" form a carbon ring group together with a carbon atom to which R' and R" are bonded), where the alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl. "k" is 0 or 1.

In General Formula 1, $X^-$ is a monovalent anion having an oxidation potential higher than a reduction potential of the dication of General Formula 1 by 3.1 V or greater (may be referred to as a "high oxidation potential anion" hereinafter).

In General Formula 1, $W^{2+}$ is a dication represented by General Formula 2.

[General Formula 2]

In General Formula 2, o, p, and q are each independently 0 or 1; and A, B, and C are each independently an arylene group that may have a substituent and has from 2 through 20 carbon atoms, or a heterocycle group.

One of notable points in the first embodiment is that the first electrochromic layer is obtained by depositing the electrochromic compound on the conductor or semiconductor nano-structures. Specifically, the high oxidation potential anion is used as an anion of the electrochromic compound, when the electrochromic compound is deposited on the conductor or semiconductor nano-structures to form the first electrochromic layer.

Comparing Examples with Comparative Examples of the present specification, a compound represented by General Formula 1 was used in Examples, when the first electrochromic layer was formed. In Comparative Examples, meanwhile, a monovalent anion having an oxidation potential that was not higher than a reduction potential of the dication in General Formula 1 by 3.1 V or greater (e.g., $Br^-$, $Cl^-$: which may be referred to as "low oxidation potential anion" hereinafter), was used instead of the anion of the compound represented by General Formula 1, when the first electrochromic layer was formed.

The electrochromic elements of Examples of the present specification could have low YI values during production of the elements owing to the high oxidation potential anion, and the state of the low YI value was maintained for a long period.

Meanwhile, the electrochromic elements of Comparative Examples of the present specification each had a high YI value during production of the elements owing to the low oxidation potential, and the state of high YI value was maintained for a long period.

Typically, ion exchange between anions in the electrolyte layer and anions in the first electrochromic layer occurs after production of an electrochromic element. The degree of the ion exchange is not known, but it is expected that ion exchange occurs at the degree of about 50% or greater. Therefore, ion exchange between the anions included in the electrolyte layer at the time of production of the device and the anions included in the first electrochromic layer at the time of production of the element is performed at a certain degree. Even in the electrochromic elements of Comparative Examples of the present specification, as a result, the anions included in the electrolyte layer are included in the first electrochromic layer after the production of the electrochromic element. Once ion exchange occurs, it is almost impossible to determine an amount of the anions exchanged based only on the electrochromic element after the ion exchange. This is because analysis cannot confirm whether the anions included in the first electrochromic layer and the anions included in the electrolyte layer in the electrochromic element after ion exchange are, or are not the anions used for forming the first electrochromic layer and the anions used for forming the electrolyte layer at the time of production of the electrochromic element, respectively.

When the electrochromic elements of Comparative Examples of the present specification were produced, the high oxidation potential anions were used for forming the electrolyte layer. In this case, once ion exchange occurs, the high oxidation potential anions are present in the first electrochromic layer of the electrochromic element of each Comparative Example after the ion exchange, but the state of the YI value high enough to distinguish from the YI value of each Example was maintained.

In both Examples and Comparative Examples of the present specification, therefore, there was a state where the high oxidation potential anions were included in the first electrochromic layer after the production of the electrochromic element, but the states of the electrochromic elements of Examples and the states of the electrochromic elements of Comparative Examples were clearly different in terms of the YI values. However, it is impossible or unrealistic for a small-size electrochromic element having a thin first electrochromic layer and a thick electrolyte layer relative to the thickness of the first electrochromic layer to distinguish, through an analysis, the states having the high oxidation potential anions in the first electrochromic layers after production of the electrochromic elements, both in Examples and Comparative Examples of the present specification. The fact that such analysis is impossible or unrealistic is clear from that, for example, it is impossible to analyze a difference between the following 2 devices (a first device and a second device) after the devices are produced and ion exchange is performed.

First element: An element, which uses 1 unit of the high oxidation potential anion for forming a first electrochromic layer, and uses a mixture of the high oxidation potential anion and the low oxidation potential anion (a mixture of 50 units: 50 units) for forming an electrolyte layer at the time of production of the element.

Second element: An element, which uses 1 unit of the low oxidation potential anion for forming a first electrochromic layer, and uses a mixture of the high oxidation potential anion and the low oxidation potential anion (a mixture of 49 units: 51 units) for forming an electrolyte layer at the time of production of the element.

After ion exchange of about 50% or greater between anions of the first electrochromic layer and anions of the electrolyte layer in each of the first element and the second element, a difference in the amounts of the high oxidation potential anion and the second oxidation potential anion present in the first electrochromic layer and the electrolyte layer between the first device and the second device cannot be distinguished.

Accordingly, one of the notable points in the first embodiment is that the first electrochromic layer is formed by depositing the electrochromic compound on the conductor or semiconductor nano-structures. Specifically, the notable point is that the high oxidation potential anion is used as an anion of the electrochromic compound, when a first electrochromic layer is formed by depositing the electrochromic compound on the conductor or semiconductor nano-structures. The above-described point is particularly notable when anions used for forming an electrolyte layer is not particularly limited.

Second Embodiment

A second embodiment of the electrochromic element of the present disclosure includes a first electrode, a second electrode disposed to face the first electrode with a gap between the first electrode and the second electrode, a first electrochromic layer disposed on or above the first electrode, where the first electrochromic layer includes conductor or semiconductor nano-structures and an electrochromic compound, and an electrolytelayer including an electrolyte, disposed between the first electrochromic layer and the second electrode. The electrochromic compound is a compound represented by General Formula 1 below. An anion of the electrolyte is a monovalent anion having an oxidation potential that is higher than a reduction potential of the dication of General Formula 1 by 3.1 V or greater.

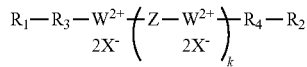

[General Formula 1]

In General Formula 1, $R_1$ and $R_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, or a functional group that can bond to a hydroxyl group; $R_3$ and $R_4$ are each an alkylene group having from 1 through 10 carbon atoms or an arylene group that may have a substituent and has 12 or less carbon atoms.

In General Formula 1, Z is alkylene, cycloalkylene, or a divalent group represented by —$R_7$—Y—$R_8$ (where $R_7$ and $R_8$ are each independently a single bond, alkylene, or cycloalkylene, and Y is arylene, cycloalkylene, heteroarylene, arylene-arylene, or arylene-CR'R"-arylene, where R' and R" form a carbon ring group together with a carbon atom to which R' and R" are bonded), where the alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl; and k is 0 or 1.

In General Formula 1, X⁻ is a monovalent anion having an oxidation potential higher than a reduction potential of the dication of General Formula 1 by 3.1 V or greater.

In General Formula 1, $W^{2+}$ is a dication represented by General Formula 2.

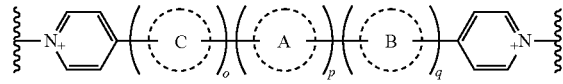

[General Formula 2]

In General Formula 2, o, p, and q are each independently 0 or 1; and A, B, and C are each independently an arylene group that may have a substituent and has from 2 through 20 carbon atoms, or a heterocycle group.

According to the second embodiment, a device having excellent transparency can be obtained even when anions of an electrochromic compound and anions of an electrolyte are ion-exchanged within the device.

In the second embodiment, the first electrochromic layer includes conductor or semiconductor nano-structures, and an electrochromic compound on or above the first electrode.

In the second embodiment, the first electrochromic layer is not particularly limited and may be appropriately selected depending on the intended purpose, as long as the first electrochromic layer includes conductor or semiconductor nano-structures and the electrochromic compound. The first electrochromic layer is preferably an electrochromic layer in a state where the electrochromic compound is deposited on the conductor or semiconductor nano-structures. In other words, in the second embodiment, the first electrochromic layer is preferably an electrochromic layer in which the electrochromic compound is deposited on the conductor or semiconductor nano-structures.

The following 2 points are some of the notable points in the second embodiment.

(i) The electrochromic compound of the first electrochromic layer is a compound represented by General Formula 1.

(ii) An anion of an electrolyte in an electrolyte layer including the electrolyte is a monovalent anion having an oxidation potential higher than a reduction potential of the dication in General Formula 1 by 3.1 V or greater.

In the first embodiment, it is desired that the high oxidation potential anion is used as an anion of the electrochromic compound when the electrochromic layer is deposited on the conductor or semiconductor nano-structure to form a first electrochromic layer. It is particularly desirable when anions used for forming an electrolyte layer are not limited.

In the second embodiment, meanwhile, in addition to that the electrochromic compound of the first electrochromic layer is a compound represented by General Formula 1, an anion of an electrolyte in an electrolyte layer is the high oxidation potential anion. In this case, anions present in the first electrochromic layer and electrolyte layer are only the anions of high oxidation potential. Even if ion exchange between the anions occurs, therefore, a state of the high oxidation potential anion present in the first electrochromic layer and a state of the high oxidation potential anion present in the electrolyte layer hardly change.

In the second embodiment, the electrochromic compound in the first electrochromic layer is a compound represented by General Formula 1 and an anion of the electrolyte is a monovalent anion having an oxidation potential higher than a reduction potential of the dication in General Formula 1 by 3.1 V or greater before or after anion exchange is performed between the first electrochromic layer and the electrolyte layer.

In the second embodiment, the electrolyte layer may include the low oxidation potential anion in a trace up to about 10 mol % relative to a total amount of anions, and the first electrochromic layer may include the low oxidation potential anion in a trace up to about 10 mol % relative to a total amount of anions.

<First Electrochromic Layer>

In the first embodiment, the first electrochromic layer is formed by depositing the electrochromic compound on the conductor or semiconductor nano-structures.

In the second embodiment, the first electrochromic layer includes conductor or semiconductor nano-structures, and an electrochromic compound. In the second embodiment, moreover, the first electrochromic layer is preferably formed by depositing an electrochromic compound on conductor or semiconductor nano-structures.

In the present specification, the term "deposited" or "depositing" means a chemically bonded state, such as via a covalent bond and an ionic bond, a physically adsorbed state due to a hydrogen bond or intermolecular forces, or a state where particles or amorphous solids are physically deposited. However, the state of "deposited" or "depositing" is not limited to the above-listed examples.

As a formation method of the first electrochromic layer, for example, vacuum vapor deposition, sputtering, ion plating, etc., can be used. In the case where a material of the first electrochromic layer is a material that can be formed by coating, usable are various printing methods, such as spin coating, casting, microgravure coating, gravure coating, bar coating, roll coating, wire bar coating, dip coating, slit coating, capillary coating, spray coating, nozzle coating, gravure printing, screen printing, flexo printing, offset printing, reverse printing, and inkjet printing.

For example, a first electrochromic layer, in which an electrochromic compound is deposited on conductor or semiconductor nano-structures, can be formed by forming a first electrochromic layer according to the method disclosed in Examples of the present specification.

The average thickness of the first electrochromic layer is not particularly limited and may be appropriately selected depending on the intended purpose. The average thickness thereof is preferably 0.2 µm or greater but 5.0 µm or less. When the average thickness thereof is 0.2 µm or greater, high coloring density can be obtained. When the average thickness thereof is 5.0 µm or less, a production cost can be kept low, and visibility tends not to deteriorate due to coloring. The first electrochromic layer can be formed of a vacuum deposition film, but the first electrochromic layer is preferably formed by applying a particle dispersion paste in view of productivity.

The first electrochromic layer is disposed on or above the first electrode. Only one layer thereof may be disposed, or two or more layers thereof may be disposed.

The electrochromic compound may be deposited after forming the conductor or semiconductor nano-structures. In this case, a formation method of the conductor or semiconductor nano-structure may be the same as the formation method of the first electrochromic layer. As a deposition method of the electrochromic compound, for example, vacuum vapor deposition, sputtering, ion plating, etc., can be used. Moreover, usable are various printing method, such as spin coating, casting, microgravure coating, gravure coating, bar coating, roll coating, wire bar coating, dip coating, slit coating, capillary coating, spray coating, nozzle coating, gravure printing, screen printing, flexo printing, offset printing, reverse printing, and inkjet printing.

<<Conductor or Semiconductor Nano-Structures>>

The conductor or semiconductor nano-structures of the present disclosure are structures having irregularities of nano-scale, such as nano particles, and nano-porous structures.

A material constituting the conductor or semiconductor nano-structure is preferably metal oxide in view of transparency and conductivity. Examples of the metal oxide include metal oxides each including, as a main component, titanium oxide, zinc oxide, tin oxide, zirconium oxide, cerium oxide, yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, aluminosilicate, calcium phosphate, or aluminosilicate. Moreover, the above-listed metal oxides may be used alone or in combination.

Considering electric properties, such as electrical conductivity, and physical properties, such as optical properties, response speed for coloring and bleaching is excellent when at least one selected from the group consisting of metal oxides, such as titanium oxide, zinc oxide, tin oxide, zirconium oxide, iron oxide, magnesium oxide, indium oxide, and tungsten oxide, or a mixture thereof, is used. Particularly, response speed for coloring and bleaching is excellent when titanium oxide is used.

As a shape of the metal oxide, preferable are metal oxide particles having the average primary particle diameter of 30 nm or less. Light transmittance of metal oxide improves as the particle diameter is smaller. A shape thereof giving a large surface area per unit volume (referred to as "specific surface area" hereinafter) is used. Since the metal oxide particles have a large specific surface area, the electrochromic compound is more efficiently born thereon, and a resultant device enables a multi-color display having an excellent display contrast ratio between coloring and bleaching. The specific surface area of the nano structure is not particularly limited. For example, the specific surface area thereof is 100 m²/g or greater.

<<Electrochromic Compound>>

The electrochromic compound of the present disclosure is a compound represented by General Formula 1 below.

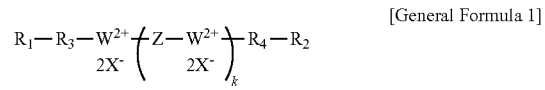

[General Formula 1]

In General Formula 1, $R_1$ and $R_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, or a functional group that can bond to a hydroxyl group; and $R_3$ and $R_4$ are each an alkylene group having from 1 through 10 carbon atoms or an arylene group that may have a substituent and has 12 or less carbon atoms.

In General Formula 1, Z is alkylene, cycloalkylene, or a divalent group represented by —$R_7$—Y—$R_8$ (where $R_7$ and $R_8$ are each independently a single bond, alkylene, or cycloalkylene, and Y is arylene, cycloalkylene, heteroarylene, arylene-arylene, or arylene-CR'R"-arylene, where R' and R" form a carbon ring group together with a carbon atom to which R' and R" are bonded), where the alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl; and k is 0 or 1.

In General Formula 1, $X^-$ is a monovalent anion having an oxidation potential higher than a reduction potential of the dication of General Formula 1 by 3.1 V or greater.

In General Formula 1, $W^{2+}$ is a dication represented by General Formula 2.

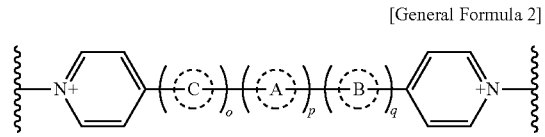

[General Formula 2]

In General Formula 2, o, p, and q are each independently 0 or 1; and A, B, and C are each independently an arylene group that may have a substituent and has from 2 through 20 carbon atoms, or a heterocycle group.

In General Formula, $W^{2+}$ is a site that exhibits an electrochromic function and causes color changes owing to oxidation and reduction of the site. $R_1$, $R_2$, $R_3$, $R_4$ and Z do not contribute to the electrochromic function and also do not hinder the electrochromic function of $W^{2+}$.

The more preferred embodiment is that at least either $R_1$ or $R_2$ is a functional group that can bond to a hydroxyl group. According to the more preferred embodiment, the electrochromic compound can be easily deposited on the conductor or semiconductor nano-structures.

The further more preferred embodiment is that both $R_1$ and $R_2$ are each a functional group that can bond to a hydroxyl group. According to the further more preferred embodiment, the bond formed becomes even stronger and therefore the electrochromic compound is less likely to be detached in the element, leading to improved reliability.

Another preferable embodiment is that $R_1$ or $R_2$ is a functional group that can bond to a hydroxyl group. According to the above-mentioned embodiment, the larger amount of the electrochromic compound can be deposited on the conductor or semiconductor nano-structures, leading to improved coloring density.

Examples of the functional group that can bond to a hydroxyl group include a phosphonic acid group, a phosphoric acid group, a carboxylic acid group, a sulfonyl group, a silyl group, and a silanol group. Among the above-listed examples, a phosphonic acid group, a phosphoric acid group, and a carboxylic acid group are preferable, and a phosphonic acid group is more preferable in view of easiness of synthesis, adsorption of the electrochromic compound to bearing particles, and stability of the electrochromic compound.

Examples of the silyl group include the following alkoxysilyl group.

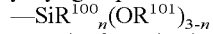
—$SiR^{100}{}_n(OR^{101})_{3-n}$

In the formula above, $R^{100}$ is an alkyl group having from 1 through 4 carbon atoms, and $R^{101}$ is an alkoxy group having from 1 through 4 carbon atoms; n is an integer of from 0 to 2. When there are two or more 100, all of $R^{100}$ may be identical or different. When there are two or more $OR^{101}$, all of $OR^{101}$ may be identical or different.

In the present disclosure, for example, $R_1$ or $R_2$, or both $R_1$ and $R_2$ are preferably a phosphonic acid group, a phosphoric acid group, a carboxylic acid group, a sulfonyl group, a silyl group, or a silanol group in General Formula 1. Use of such groups can make a resultant electrochromic compound easily deposited on the conductor or semiconductor nano-structures.

In this case, the bind between the electrochromic compound and the conductor or semiconductor nano-structures is strong, which reduces possibility for the electrochromic compound to detach from the conductor or semiconductor nano-structure in the element, and therefore reliability can be improved, for example, when $R_1$ and $R_2$ (i.e., both $R_1$ and $R_2$) are any of a phosphonic acid group, a phosphoric acid group, a carboxylic acid group, a sulfonyl group, a silyl group, or a silanol group in General Formula 1.

In the present disclosure, moreover, when one of $R_1$ or $R_2$ is any of a phosphonic acid group, a phosphoric acid group, a carboxylic acid group, a sulfonyl group, a silyl group, or a silanol group, and the the other is a hydrogen atom, an aryl group having 14 or less carbon atoms, a heteroaryl group having 14 or less carbon atoms, a branched alkyl group having 10 or less carbon atoms, an alkenyl group having 10 or less carbon atoms, or a cycloalkyl group having 10 or less carbon atoms, the larger amount of the electrochromic compound can be deposited on the conductor or semiconductor nano-structures, and therefore coloring density can be improved.

When the electrochromic compound includes, as a functional group, a phosphonic acid group, a phosphoric acid group, a carboxyl group, or a sulfonyl group, the electrochromic compound can be deposited on the nano-structures more easily. When the electrochromic compound includes a silyl group, a silanol group, etc., the electrochromic compound is deposited via a siloxane bond, and therefore the bond between the electrochromic compound and the nano-structure becomes strong. As a result, a stable electrochromic layer can be obtained. The siloxane bond is a chemical bond via a silicon atom and an oxygen atom.

Examples of the phosphonic acid group include a methyl phosphonic acid group, an ethyl phosphonic acid group, a propyl phosphonic acid group, a hexyl phosphonic acid group, an octyl phosphonic acid group, a decyl phosphonic acid group, a dodecyl phosphonic acid group, an octadecyl phosphonic acid group, a benzyl phosphonic acid group, a phenylethyl phosphonic acid group, a phenylpropyl phosphonic acid group, and a biphenyl phosphonic acid group.

Examples of the phosphoric acid group include a methyl phosphoric acid group, an ethyl phosphoric acid group, a propyl phosphoric acid group, a hexyl phosphoric acid group, an octyl phosphoric acid group, a decyl phosphoric acid group, a dodecyl phosphoric acid group, an octadecyl phosphoric acid group, a benzyl phosphoric acid group, a phenylethyl phosphoric acid group, a phenylpropyl phosphoric acid group, and a biphenyl phosphoric acid group.

Examples of the carboxylic acid group include a methyl carboxylic acid group, an ethyl carboxylic acid group, a propyl carboxylic acid group, a hexyl carboxylic acid group, an octyl carboxylic acid group, a decyl carboxylic acid group, a dodecyl carboxylic acid group, an octadecyl carboxylic acid group, a benzyl carboxylic acid group, a phenylethyl carboxylic acid group, a phenylpropyl carboxylic acid group, a biphenyl carboxylic acid group, a 4-propylphenylcarboxylic acid group, and a 4-propylbiphenylcarboxylic acid group.

Examples of the sulfonyl group include a methylsulfonyl group, an ethylsulfonyl group, a propylsulfonyl group, a hexylsulfonyl group, an octylsulfonyl group, a decylsulfonyl group, a dodecylsulfonyl group, an octadecylsulfonyl group, a benzylsulfonyl group, a phenylethylsulfonyl group, a phenylpropylsulfonyl group, and a biphenylsulfonyl group. Examples of the silyl group include a methylsilyl group, an ethylsilyl group, a propylsilyl group, a hexylsilyl group, an octylsilyl group, a decylsilyl group, a dodecylsilyl group, an octadecylsilyl group, a benzylsilyl group, a phenylethylsilyl group, a phenylpropylsilyl group, and a biphenylsilyl group. Examples of the silanol group include a methylsilanol group, an ethylsilanol group, a propylsilanol group, a hexylsilanol group, an octylsilanol group, a decylsilanol group, a dodecylsilanol group, an octadecylsilanol group, a benzylsilanol group, a phenylethylsilanol group, a phenylpropylsilanol group, and a biphenylsilanol group.

In General Formula 1, Z is preferably selected from the group consisting of C1-C12 alkylene, C3-C7 cycloalkylene, C3-C14 arylene, C5-C10 heteroarylene, (C1-C4 alkylene)-(C3-C14 arylene), (C1-C4 alkylene)-(C3-C14 heteroarylene), (C1-C4 alkylene)-(C3-C14 arylene)-(C1-C4 alkylene), (C1-C4 alkylene)-(C3-C14 heteroarylene)-(C1-C4 alkylene), (C3-C14 arylene)-(C3-C14 arylene), (C1-C4 alkylene)-(C3-C14 arylene)-(C3-C14 arylene)-(C1-C4 alkylene), and (C3-C14 arylene)-(CR'R'')—(C3-C14 arylene), where R' and R'' form a C3-C20 carbon cyclic group together with a carbon atom to which R' and R'' are bonded. The arylene and cycloalkylene group may be each substituted with one or more substituents selected from halogen, C1-C4 alkyl, C1-C4 alkoxy, and C3-C7 cycloalkyl. The alkylene group may be substituted with one or more substituents selected from halogen, C3-C14 alkyl, C1-C12 alkoxy, C2-C12 acyloxy, C1-C12 hydroxyalkyl, C3-C12 cycloalkyl, phenyl, phenyloxy, and substituted phenyl. Specifically, the substituted alkylene include —CH$_2$(CRaRb)CH$_2$—, where Ra and Rb are each independently selected from the group consisting of H, C3-C14 alkyl, C3-C12 cycloalkyl, (cycloalkyl)methyl, aryl, substituted aryl, arylalkyl (e.g., benzyl or phenyl(C2-C7 alkyl)), phenyloxyethyl, substituted arylalkyl, C1-C12 alkoxy, C2-C12 acyloxy, C1-C12 hydroxyalkyl, and C1-C12 alkoxymethyl.

Z is more preferably selected from the group consisting of C1-C12 alkylene, aryl-substituted C1-C12 alkylene, phenylene, naphthylene, (C1-C4 alkylene)-phenylene-(C1-C4 alkylene), (C1-C4 alkylene)-naphthylene-(C1-C4 alkylene) (e.g., naphthylene bis(methylene)), quinoxaline-2,3-diyl, (C1-C4 alkylene)-quinoxaline-2,3-diyl-(C1-C4 alkylene) (e.g., quinoxaline-2,3-diylbis(methylene)), phenylene-phenylene, (C1-C4 alkylene)-phenylene-phenylene-(C1-C4 alkylene) and phenylene-fluorenylene-phenylene.

Examples of Z include —CH$_2$—, —(CH$_2$)$_2$—, —(CH$_2$)$_3$—, —(CH$_2$)$_4$—, —(CH$_2$)$_5$—, —CH$_2$—CH(CH$_3$)—CH$_2$—, —CH$_2$—CH(CH$_2$phenyl)-CH$_2$—, —(CH$_2$)$_2$—CH(CH$_3$)—CH$_2$—, —(CH$_2$)$_3$—CH(CH$_3$)—CH$_2$—, and —(CH$_2$)$_2$—CH(CH$_3$)—(CH$_2$)$_2$—.

Moreover, Z in General Formula 1 is preferably any of those represented by the following structural formulae.

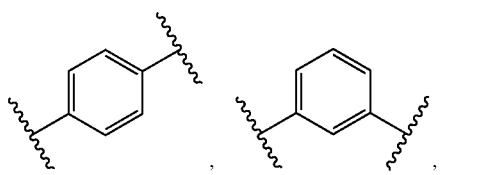,

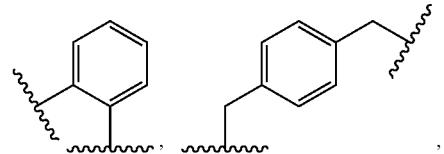,

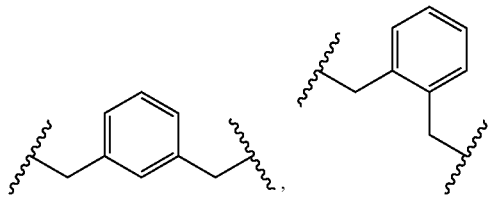,

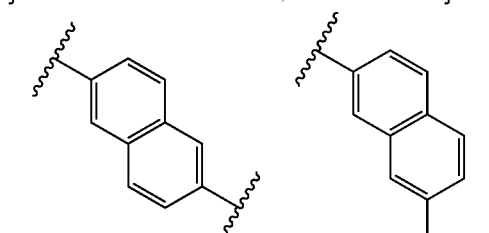,

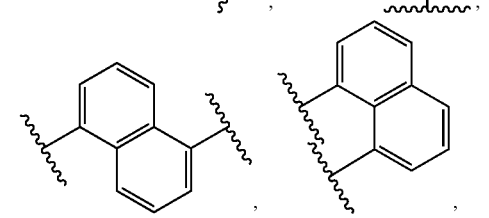,

-continued

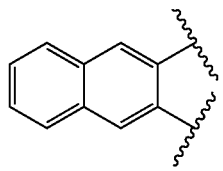,

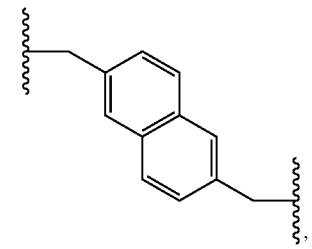,

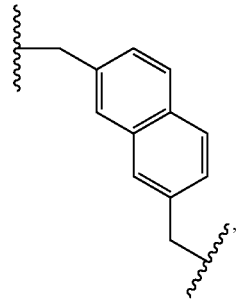,

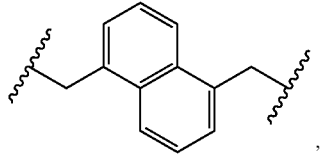,

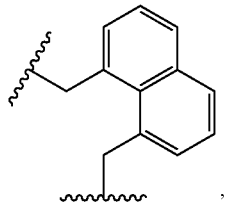,

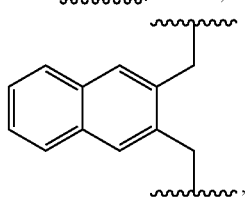,

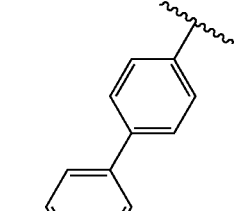,

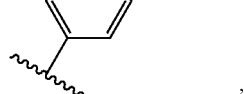,

-continued

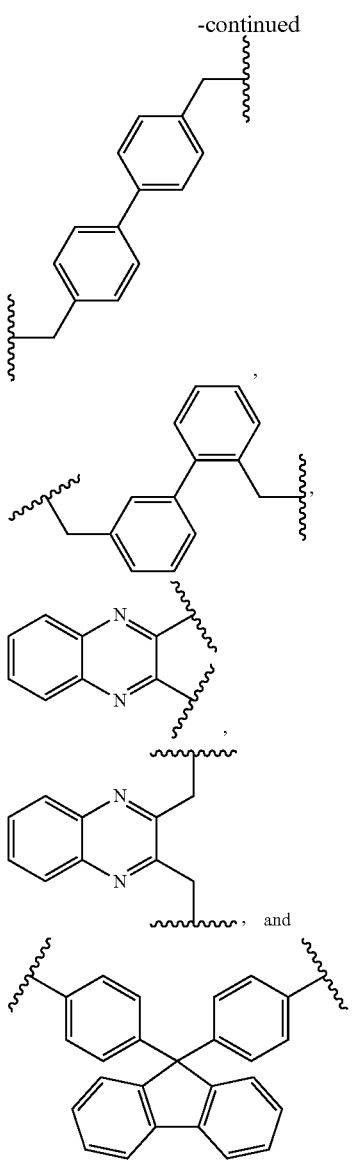

, and

The oxidation potential of $X^-$ of General Formula 1 is higher than a reduction potential of the dication of General Formula 1 by 3.1 V or greater. In other words, $X^-$ has a monovalent anion having the oxidation potential that is higher than reduction potential of the dication of General Formula 1 by 3.1 V or greater. When the oxidation potential of $X^-$ is not higher than the reduction potential of the dication of General Formula 1 by 3.1 V or greater, slight coloring may occur in a bleached state of an element, which may reduce transparency of the element. When the electrochromic compound is deposited on the conductor or semiconductor nano-structures, the anion and the dication (the dication of General Formula 1) may form a charge transfer (CT) complex and light of a certain wavelength range may be absorbed due to CT transition. When the absorption wavelength due to the CT transition is longer than 400 nm, namely, the energy level difference between the lowest unoccupied molecular orbital (LUMO) of the anion and the highest occupied molecular orbital (HOMO) of the dication is less than 3.1 eV (i.e., a potential difference between the oxidation potential of the anion and the reduction potential of the dication is less than 3.1 V), the electrochromic element is tinted when observed with naked eyes and therefore it is not preferable. In this case, reduction in transmittance especially at a short wavelength range often results in yellowing of an element.

Examples of $X^-$ achieving a potential difference of 3.1 V or greater between the oxidation potential of the anion and reduction potential of the dication include $(FSO_2)_2N^-$, $(CFSO_2)_2N^-$, $(CN)_4B^-$, $BF_4^-$, $CF_3BF_3^-$, $PF_6^-$, $ClO_4^-$, $(C_2F_5SO_2)_2N^-$, $(C_4F_9SO_2)_2N^-$, $CF_3SO_3$, $C_2F_5SO_3$, $C_4F_9SO_3$, $(C_2F_5)_3PF_3^-$, and $(CF_3SO_2)_3C^-$. The above-listed examples may be used alone or in combination.

The more preferred embodiment is that $X^-$ is at least one selected from the group consisting of $(FSO_2)_2N^-$, $(CF_3SO_2)_2N^-$, $(CN)_4B^-$, $BF_4^-$, $PF_6^-$, and $ClO_4^-$. The above-listed anions are large enough to easily form a CT complex with a dication, and are stable. Moreover, the above-listed anions are not too large so that sufficient response speed can be obtained. Therefore, an electrochromic element having excellent response as well as excellent transparency can be obtained using any of the above-listed anions.

The further more preferred embodiment is that $X^-$ is at least one selected from the group consisting of $(FSO_2)_2N^-$, and $(CF_3SO_2)_2N^-$. The above-listed anions have especially excellent stability and response, and therefore use of the above-listed anions can achieve an element having improved durability.

The most preferred embodiment is that $X^-$ is $(CF_3SO_2)_2N^-$ (may be referred to as (TFSI) hereinafter). Since $(CF_3SO_2)_2N^-$ is used, an element that can realize the higher coloring density can be obtained. A mechanism thereof is not clear, but it is considered that a distance between dication molecules or a packing structure thereof when the electrochromic compound is deposited on the nano-structures, or a deposition state, such as a surface state of the conductor or semiconductor nano-structures during the deposition process, may affect the coloring density. It is assumed that the surface state of the conductor or semiconductor nano-structures during the deposition process may change depending on wettability or pH of the electrochromic compound solution when the electrochromic compound solution is applied to the nano-structures.

The preferred embodiment of the electrochromic compound is that $W^{2+}$ in General Formula 1 is represented by Structural Formula 1 below.

According to the preferred embodiment, stability of a colored state of the dication improves, and therefore an element having improved reliability can be achieved.

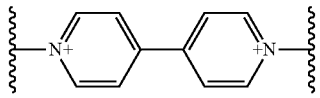

[Structural Formula 1]

Another preferred embodiment of the electrochromic compound is that k in General Formula 1 is 0. As a result, solubility of the electrochromic compound improves, and therefore a large amount of the electrochromic compound can be easily deposited on the conductor or semiconductor nano structures, leading to improvement of coloring density.

Another preferred embodiment of the electrochromic compound is that $R_3$ of General Formula 1 is represented by General Formula 3, and $R_4$ of General Formula 1 is represented by General Formula 4. According to the above-mentioned embodiments, durability of the electrochromic compound is enhanced, and an element having the higher reliability can be obtained.

[General Formula 3]

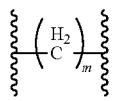

[General Formula 4]

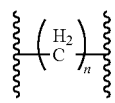

In General Formula 3, m is 0 or an integer of from 1 through 10. In General Formula 4, n is 0 or an integer of from 1 through 10. The value of m and the value of n may be identical or different.

Specific exemplary compounds of the electrochromic compound of the present disclosure are listed below, but the electrochromic compound is not limited to the following exemplary compounds.

<Exemplary Compound 1-1>

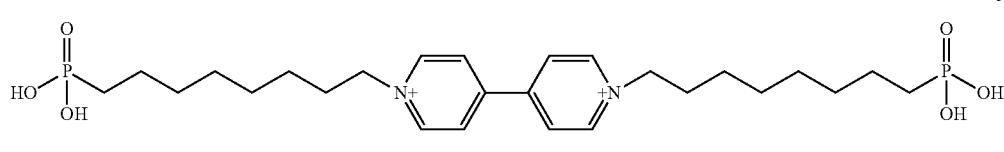

<Exemplary Compound 1-2>

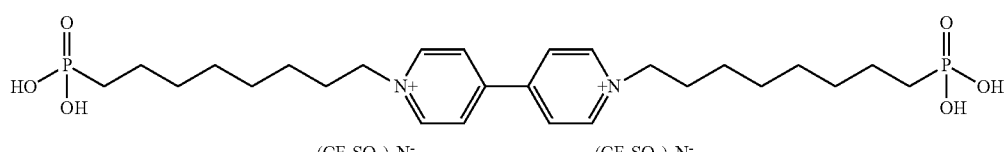

<Exemplary Compound 1-3>

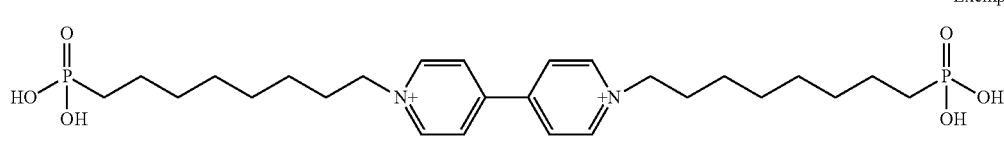

<Exemplary Compound 1-4>

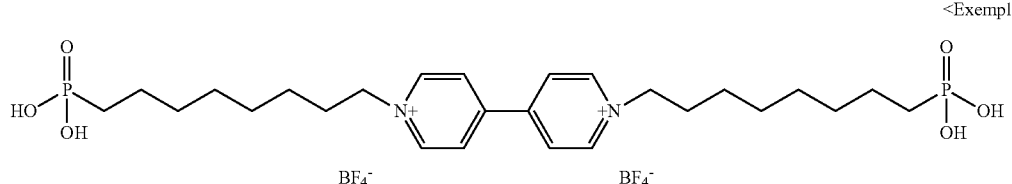

<Exemplary Compound 1-5>

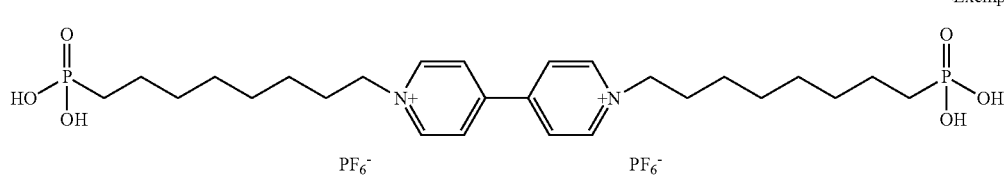

<Exemplary Compound 1-6>

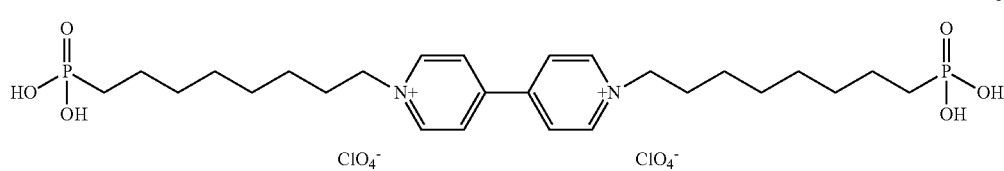

<Exemplary Compound 1-7>

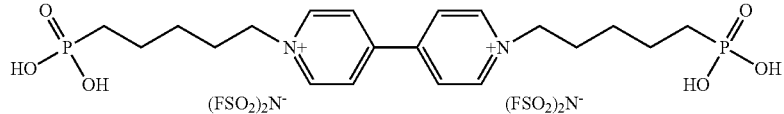

-continued
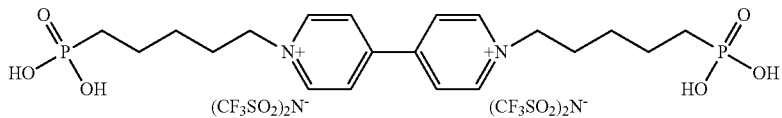
<Exemplary Compound 1-8>
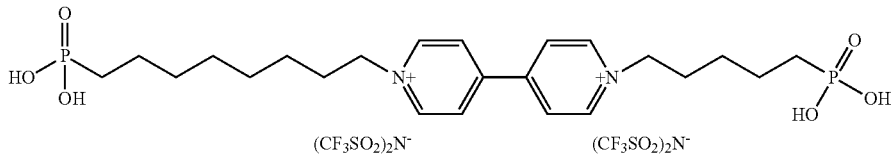
<Exemplary Compound 1-9>
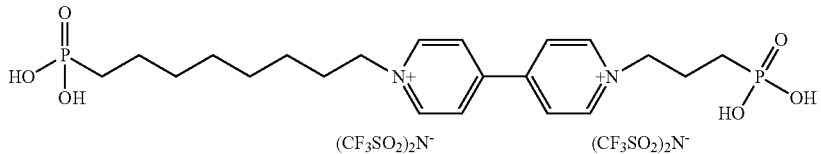
<Exemplary Compound 1-10>
<Exemplary Compound 1-11> <Exemplary Compound 1-12>
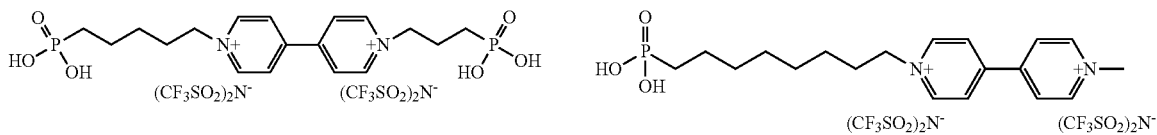
<Exemplary Compound 1-13>
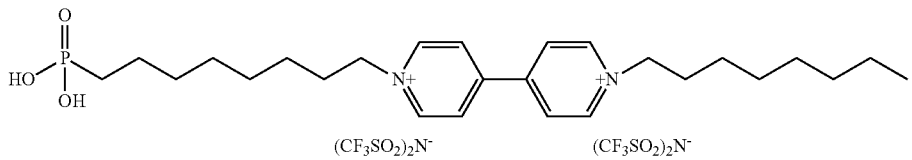
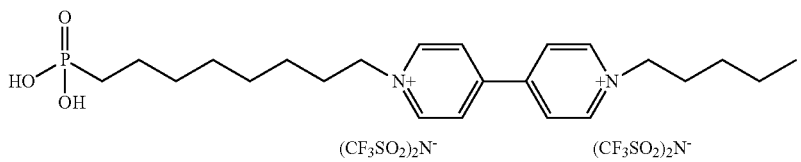
<Exemplary Compound 1-14>
<Exemplary Compound 1-15> <Exemplary Compound 1-16>
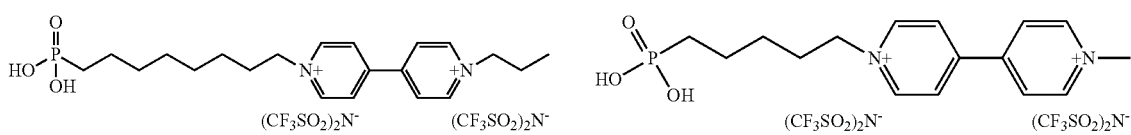
<Exemplary Compound 1-17> <Exemplary Compound 1-18>
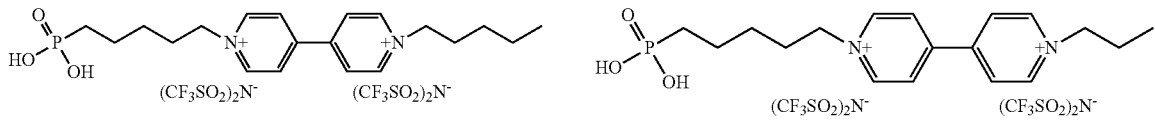
<Exemplary Compound 1-19>
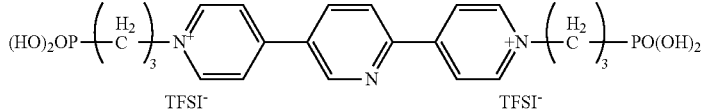
<Exemplary Compound 1-20>
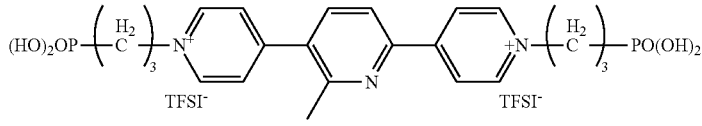

-continued
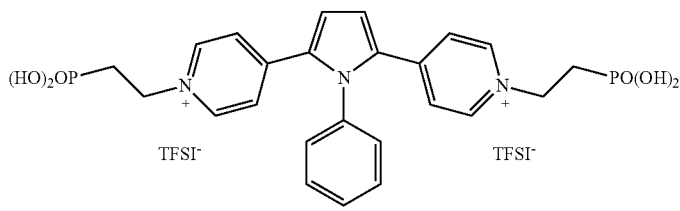
<Exemplary Compound 1-21>
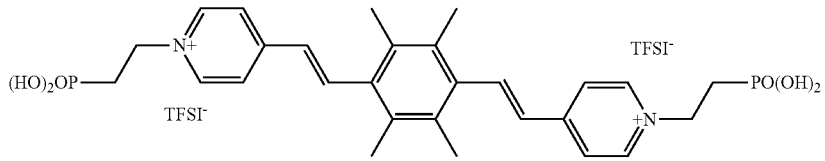
<Exemplary Compound 1-22>
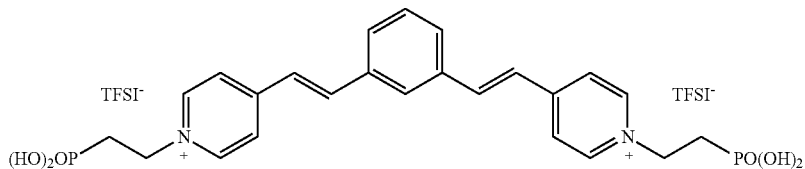
<Exemplary Compound 1-23>
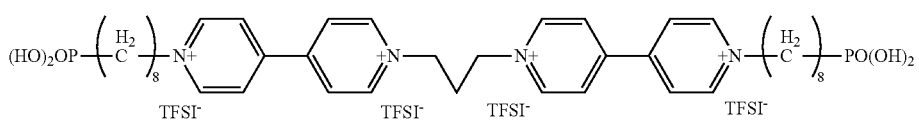
<Exemplary Compound 1-24>
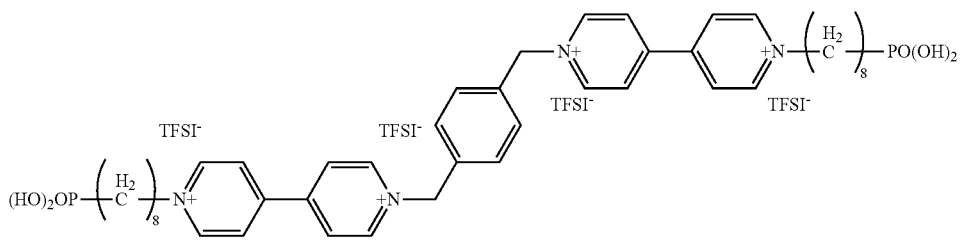
<Exemplary Compound 1-25>
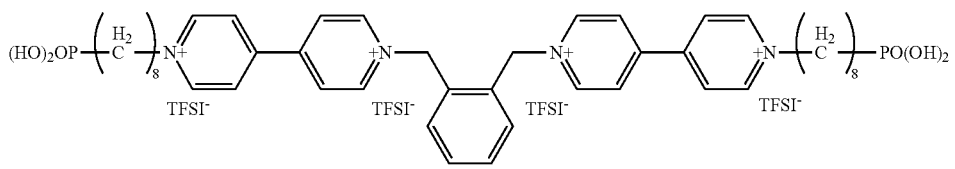
<Exemplary Compound 1-26>
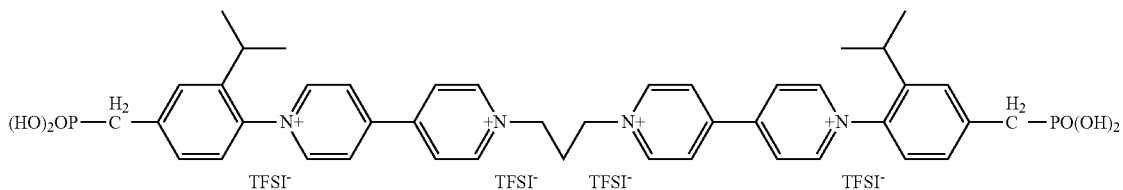
<Exemplary Compound 1-27>
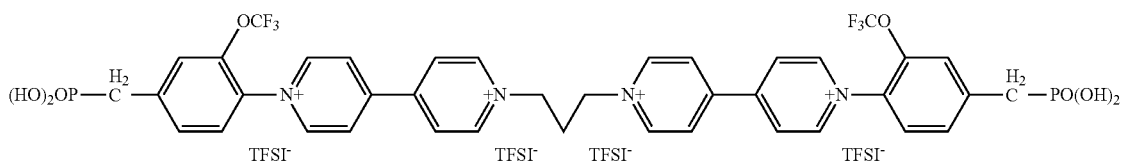
<Exemplary Compound 1-28>

-continued

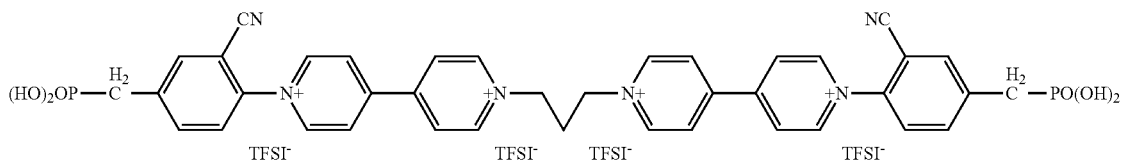
<Exemplary Compound 1-29>

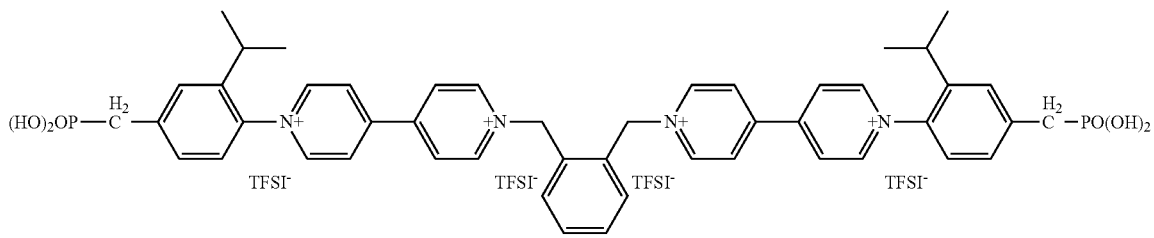
<Exemplary Compound 1-30>

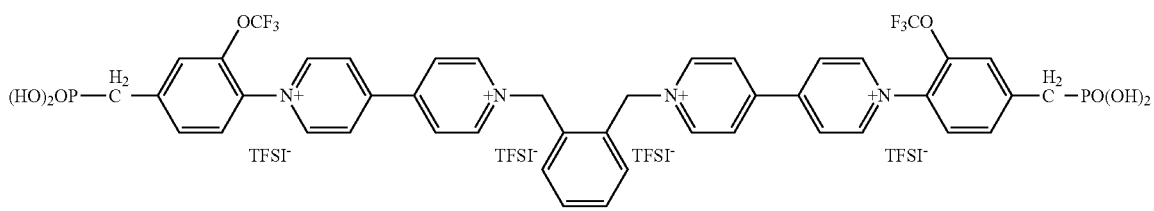
<Exemplary Compound 1-31>

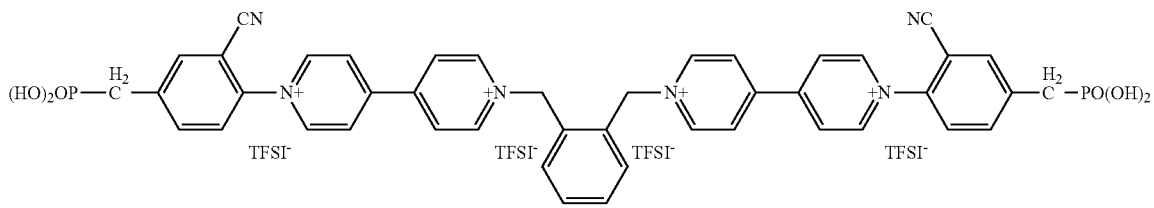
<Exemplary Compound 1-32>

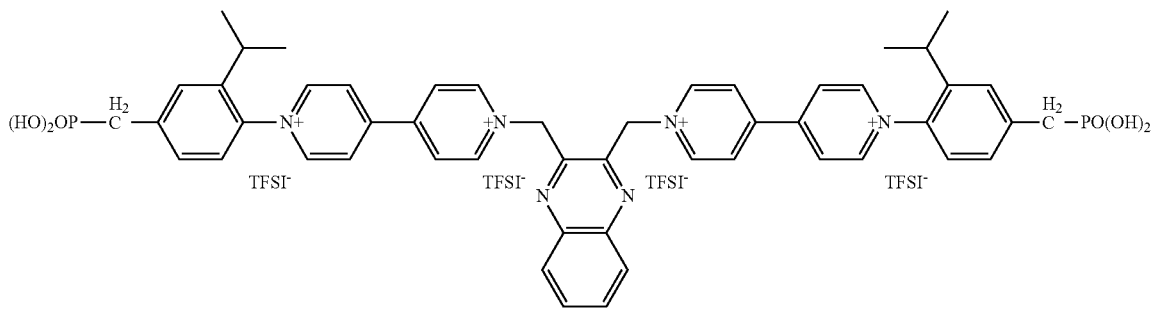
<Exemplary Compound 1-33>

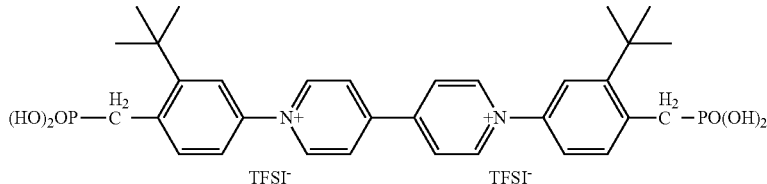
<Exemplary Compound 1-34>

As a method for confirming types of ions of the electrochromic layer, various methods known in the art can be used. Particularly, ion chromatography is effective.

One example of the confirmation method is a method where the electrochromic element is dismantled to expose the electrochromic layer, the electrochromic layer is washed with a solvent (e.g., water and alcohol), or immersed in a solvent to allow the electrochromic compound to be dissolved in the solvent. In this method, heating, or a hydrolysis treatment by adding acid or alkali may be optionally performed in combination. In order to prevent contamination with ions of the electrolyte layer, the electrochromic compound may be dissolved in the above-described manner after washing the electrochromic layer in advance. The type of ion can be identified by analyzing the solution obtained in the above-described manner by ion chromatography.

However, attentions need to be paid because there is a possibility that there is a trace of impurity contamination, such as $OH^-$ and halogenated ions, from the atmosphere or other members during the operation of the analysis.

The oxidation potential of $X^-$ can be measured according to methods known in the art. In the case where the measurement is performed electrochemically, for example, a measurement method is preferably matched to a measurement method when reduction potential of the electrochromic compound is measured. Specifically, it is preferred that a work electrode, counter electrode, reference electrode, solvent, electrolyte, measuring conditions for used be identical in the both methods. When oxidation and reduction potentials are measured by cyclic voltammetry, first, the electrode potential is swept to the direction of reduction to measure a reduction potential of the electrochromic compound of the present disclosure, followed by sweeping the electrode potential straight to the direction of oxidation to measure an oxidation potential of $X^-$. The oxidation and reduction potentials are easily measured by cyclic voltammetry because reaction potentials can be compared in the same system. When an oxidation potential of $X^-$ cannot be measured at the same time in the same system due to solubility to a solvent, or a potential window of the measuring system, a salt using a cation having a high potential window of the oxidation side is used as a counter cation of $X^-$ is prepared, and an oxidation potential of the salt is measured to measure the oxidation potential of $X^-$. However, it is often a case that there are not many measuring systems having a wide potential window up to the potential that is higher than the reduction potential of the electrochromic compound of the present disclosure by 3.1 V or greater. Therefore, it is advisable that an oxidation potential is estimated by comparing with a background current value of the same measuring system that does not include a salt of $X^-$.

<Second Electrochromic Layer>

The electrochromic element of the present disclosure preferably further includes a second electrochromic layer disposed on or above the second electrode. The second electrochromic layer includes a second electrochromic compound.

Note that, the second electrochromic layer including the second electrochromic compound means an embodiment that the second electrochromic compound is present as a constitutional component of a polymer, as well as an embodiment that the second electrochromic compound is present in the second electrochromic layer with maintaining the structure of the second electrochromic compound.

In other words, the second electrochromic layer including the second electrochromic compound means the second electrochromic layer including, as a constitutional component, the second electrochromic compound.

Since the second electrochromic layer is disposed, the two electrochromic layers are colored and bleached. Therefore, the higher coloring density can be obtained.

The second electrochromic layer is disposed on or above the second electrode. One layer thereof may be disposed, or two or more layers thereof may be disposed.

<<Second Electrochromic Compound>>

The second electrochromic compound is nor particularly limited. Any of electrochromic compounds known in the art can be used as the second electrochromic compound.

Specifically, a low-molecular weight organic electrochromic compound (e.g., an azobenzene-based compound, an anthraquinone-based compound, a diarylethene-based compound, a dihydroprene-based compound, a styryl-based compound, a styrylspiropyran-based compound, a spirooxazine-based compound, a spirothiopyran-based compound, a thioindigo-based compound, a tetrathiafulvalene-based compound, a terephthalic acid-based compound, a triphenylmethane-based compound, a triphenylamine-based compound, a naphthopyran-based compound, a viologen-based compound, a pyrazoline-based compound, a phenazine-based compound, a phenylenediamine-based compound, a phenoxazine-based compound, a phenothiazine-based compound, a phthalocyanine-based compound, a fluoran-based compound, a fulgide-based compound, a benzopyran-based compound, and metallocene-based compound), or a conductive polymer compound (e.g., polyaniline, and polythiophene) is used as the electrochromic compound. The above-listed examples may be used alone or in combination.

The second electrochromic layer more preferably includes a polymer obtained by polymerizing a polymerizable material including a radical-polymerizable compound having a triarylamine skeleton. When the second electrochromic layer includes the polymer, an electrochromic element having excellent durability can be obtained.

Preferably, the second electrochromic layer substantially consists of the polymer. The term "substantially consists of" means that the second electrochromic layer can include components other than the polymer as long as the above-described effect is not adversely affected.

The second electrochromic layer yet more preferably includes a polymer obtained by polymerizing a polymerizable material including a radical-polymerizable compound having a triarylamine skeleton and a radical-polymerizable compound having a tetraarylbenzidine skeleton. When the second electrochromic layer includes the above-mentioned polymer, an electrochromic element having excellent durability can be obtained.

The radical-polymerizable compound having a triarylamine skeleton and the radical-polymerizable compound having a tetraarylbenzidine skeleton are desirable for imparting an electrochromic function using redox reactions occurred at a surface of the second electrode. Examples of the radical-polymerizable compound having a triarylamine skeleton include compounds represented by General Formula 5 below.

$$An-Bm \qquad \text{[General Formula 5]}$$

In General Formula 5, m is 0 when n=2, and m is 0 or 1 when n=1; at least either A or B includes a radical-polymerizable functional group, where A is a structure represented by General Formula 6 below and is bonded to B at any of the positions of $R_1$ to $R_1$; and B is a structure represented by General Formula 7 and is bonded to A at any of the positions of $R_{16}$ to $R_{21}$.

Among compounds represented by General Formula 5, the radical-polymerizable compound having a tetraarylbenzidine skeleton is a compound represented by General Formula 5 where n=2.

[General Formula 6]

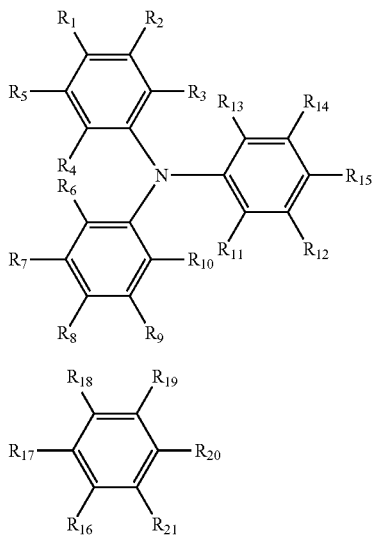

[General Formula 7]

In General Formulae 6 and 7, $R_1$ and $R_{21}$ are each a monovalent group, and may be identical or different, where at least one of the monovalent groups is a radical-polymerizable functional group.

—Monovalent Group—

Examples of each of the monovalent groups in General Formula 6 and General Formula 7 include a hydrogen atom, a halogen atom, a hydroxyl group, a nitro group, a cyano group, a carboxyl group, an alkoxycarbonyl group that may have a substituent, an aryloxycarbonyl group that may have a substituent, an alkylcarbonyl group that may have a substituent, an arylcarbonyl group that may have a substituent, an amide group, a monoalkylaminocarbonyl group that may have a substituent, a dialkylaminocarbonyl group that may have a substituent, a monoarylaminocarbonyl group that may have a substituent, a diarylaminocarbonyl group that may have a substituent, a sulfonic acid group, an alkoxysulfonyl group that may have a substituent, an aryloxysulfonyl group that may have a substituent, an alkylsulfonyl group that may have a substituent, an arylsulfonyl group that may have a substituent, a sulfone amide group, a monoalkylaminosulfonyl group that may have a substituent, a dialkylaminosulfonyl group that may have a substituent, a monoarylaminosulfonyl group that may have a substituent, a diarylaminosulfonyl group that may have a substituent, an amino group, a monoalkylamino group that may have a substituent, a dialkylamino group that may have a substituent, an alkyl group that may have a substituent, an alkenyl group that may have a substituent, an alkynyl group that may have a substituent, an aryl group that may have a substituent, an alkoxy group that may have a substituent, an aralkyl group that may have a substituent, an aryloxy group that may have a substituent, an alkylthio group that may have a substituent, an arylthio group that may have a substituent, and a heterocyclic group that may have a substituent. Among the above-listed examples, an alkyl group, an alkoxy group, a hydrogen atom, an aryl group, an aryloxy group, a halogen atom, an alkenyl group, and an alkynyl group are particularly preferable in view of stable operation.

Examples of the halogen atom include a fluorine atom, a chlorine atom, a bromine atom, and an iodine atom. Examples of the alkyl group include a methyl group, an ethyl group, a propyl group, and a butyl group. Examples of the aryl group include a phenyl group, and a naphthyl group. Examples of the aralkyl group include a benzyl group, a phenethyl group, and a naphthylmethyl group. Examples of the alkoxy group include a methoxy group, an ethoxy group, and a propoxy group. Examples of the aryloxy group include a phenoxy group, a 1-naphthyloxy group, a 2-naphthyloxy group, a 4-methoxyphenoxy group, and a 4-methylphenoxy group. Examples of the heterocyclic group include carbazole, dibenzofuran, dibenzothiophene, oxadiazole, and thiadiazole.

Examples of a substituent further substituting the substituent include a halogen atom, a nitro group, a cyano group, an alkyl group (e.g., a methyl group, and an ethyl group), an alkoxy group (e.g., a methoxy group, and an ethoxy group), an aryloxy group (e.g., a phenoxy group), an aryl group (e.g., a phenyl group, and a naphthyl group), and an aralkyl group (e.g., a benzyl group, and a phenethyl group).

—Radical-Polymerizable Functional Group—

The radical-polymerizable functional group is not particularly limited as long as the radical-polymerizable functional group is a group that has a carbon-carbon double bond and can undergo radical polymerization. Examples of the radical-polymerizable functional group include a 1-substituted ethylene functional group and a 1,1-substituted ethylene functional group presented below.

Examples of the (1) 1-substituted ethylene functional group include functional groups represented by General Formula (i) below.

   General Formula (i)

In General Formula (i), $X_1$ is an arylene group that may have a substituent, an alkenylene group that may have a substituent, a —CO— group, a —COO— group, a —CON($R_{100}$)— group [$R_{100}$ is a hydrogen atom, an alkyl group, an aralkyl group, or an aryl group], or a —S— group.

Examples of the arylene group of General Formula (i) include a phenylene group that may have a substituent, and a naphthylene group. Examples of the alkenylene group include an ethenylene group, a propenylene group, and a butenylene group. Examples of the alkyl group include a methyl group and an ethyl group. Examples of the aralkyl group include a benzyl group, a naphthylmethyl group, and a phenethyl group. Examples of the aryl group include a phenyl group and a naphthyl group.

Specific examples of the radical-polymerizable functional group represented by General Formula (i) include a vinyl group, styryl group, a 2-methyl-1,3-butadienyl group, a vinylcarbonyl group, an acryloyl group, an acryloyloxy group, an acryloylamide group, and a vinyl thioether group.

Examples of the (2) 1,1-substituted ethylene functional group include functional groups represented by General Formula (ii) below.

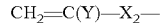   General Formula (ii)

In General Formula (ii), Y is an alkyl group that may have a substituent, an aralkyl group that may have a substituent, an aryl group that may have a substituent, a halogen atom, a cyano group, a nitro group, an alkoxy group, or a —COO$R_{101}$ group [$R_{101}$ may be a hydrogen atom, an alkyl group that may have a substituent, an aralkyl group that may have a substituent, an aryl group that may have a substituent, or CON$R_{102}R_{103}$ ($R_{102}$ and $R_{103}$ are each a hydrogen atom, an alkyl group that may have a substituent, an aralkyl group that may have a substituent, or an aryl group that may have a substituent, and $R_{102}$ and $R_{103}$ may be identical or different)]; and $X_2$ is a substituent or single bond identical to $X_1$ of General Formula (i), or an alkylene group, with the proviso that Y or $X_2$, or both are each an oxycarbonyl group, a cyano group, an alkenylene group, or an aromatic ring.

Examples of the aryl group of General Formula (ii) include a phenyl group and a naphthyl group. Examples of the alkyl group include a methyl group and an ethyl group. Examples of the alkoxy group include a methoxy group and an ethoxy group. Examples of the aralkyl group include a benzyl group, a naphthylmethyl group, and a phenethyl group.

Specific examples of the radical-polymerizable functional group represented by General Formula (ii) include an α-chloroacryloyloxy group, a methacryloyl group, a methacryloyloxy group, an α-cyanoethylene group, an α-cyanoacryloyloxy group, an α-cyanophenylene group, and a methacryloylamino group.

Examples of a substitute further substituting the substituents of $X_1$, $X_2$, and Y include a halogen atom, a nitro group, a cyano group, an alkyl group (e.g., a methyl group and an ethyl group), an alkoxy group (e.g., a methoxy group and an ethoxy group), an aryloxy group (e.g., a phenoxy group), an aryl group (e.g., a phenyl group, and a naphthyl group), and an aralkyl group (e.g., a benzyl group, and a phenethyl group).

Among the above-listed radical-polymerizable functional groups, an acryloyloxy group and a methacryloyloxy group are particularly preferable.

Preferable examples of the radical-polymerizable compound having a triarylamine skeleton include compounds represented by General Formulae (2-1) to (2-3) below.

[General Formula (2-1)]

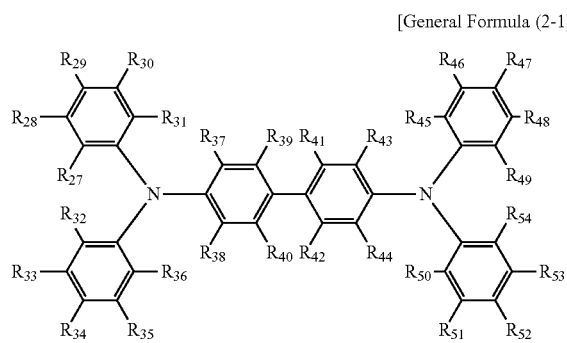

[General Formula (2-2)]

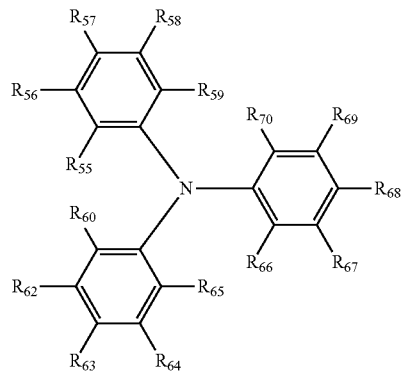

[General Formula (2-3)]

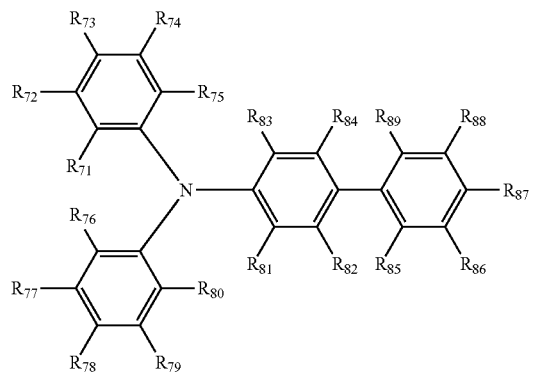

In General Formulae (2-1) to (2-3), $R_{27}$ to $R_{89}$ are each a monovalent group and may be identical or different from each other, where at least one of the monovalent groups is a radical-polymerizable functional group. Examples of the monovalent groups and the radical-polymerizable functional group include those of General Formula 5.

Among the above-listed examples, the compound represented by General Formula (2-1) is the radical-polymerizable compound having a tetraarylbenzidine skeleton.

Examples of the exemplary compounds represented by General Formula 5, and General Formulae (2-1) to (2-3) include the exemplary compounds below. The radical-polymerizable compound having a triarylamine skeleton and the radical-polymerizable compound having a tetraarylbenzidine skeleton are not limited to the following exemplary compounds.

<Exemplary Compound 3-1>

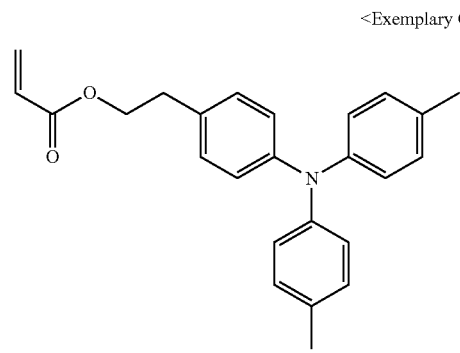

<Exemplary Compound 3-2>

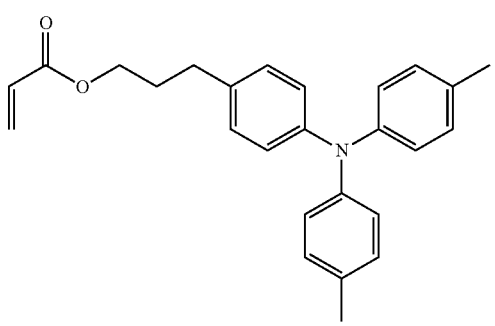

<Exemplary Compound 3-3>
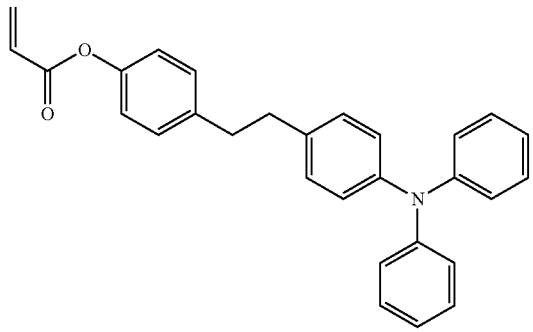
<Exemplary Compound 3-4>
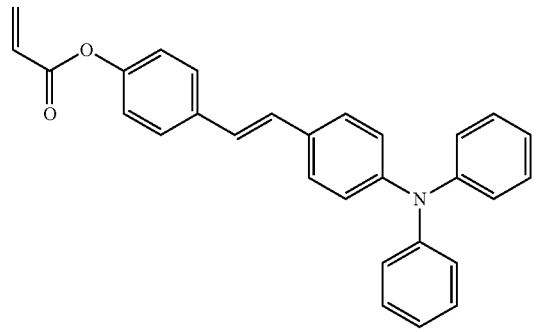
<Exemplary Compound 3-5>
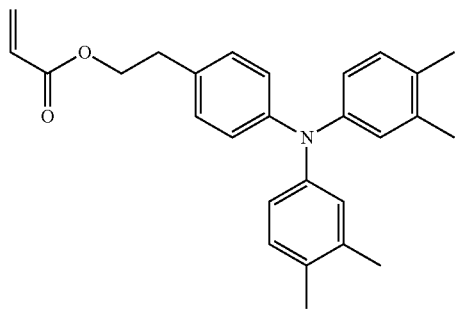
<Exemplary Compound 3-6>
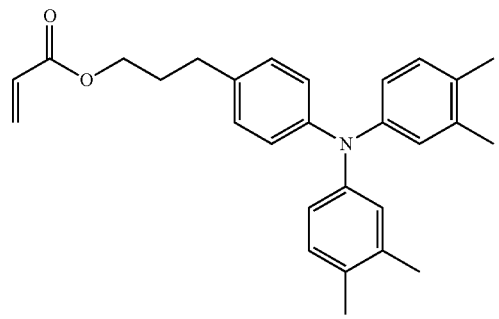
<Exemplary Compound 3-7>
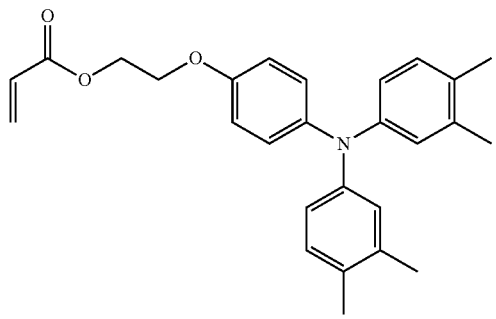
<Exemplary Compound 3-8>
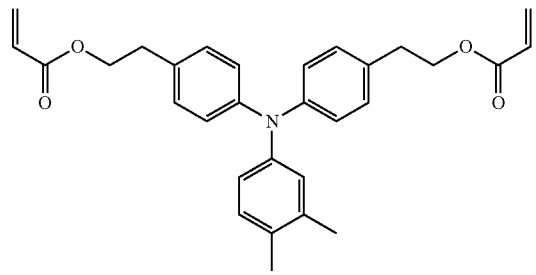
<Exemplary Compound 3-9>
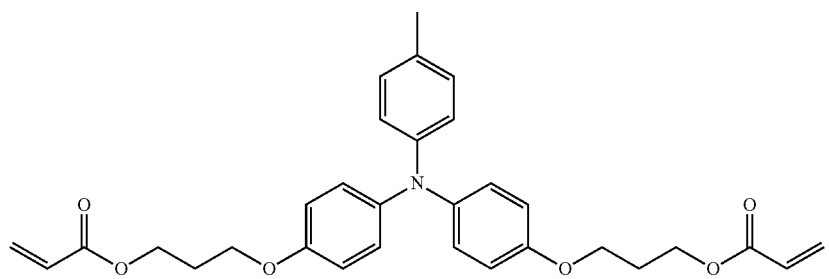

<Exemplary Compound 3-10>
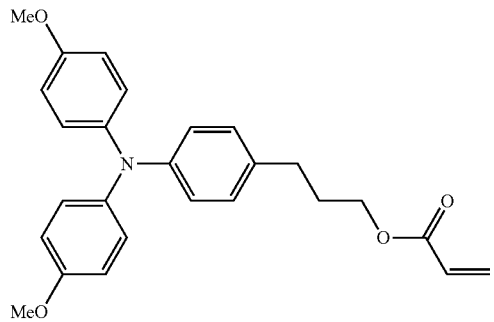
"Me" represents a methyl group.
<Exemplary Compound 3-11>
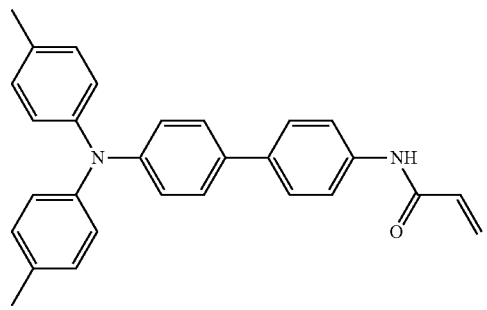
<Exemplary Compound 3-12>
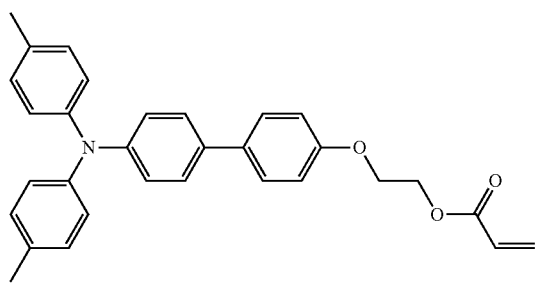
<Exemplary Compound 3-13>
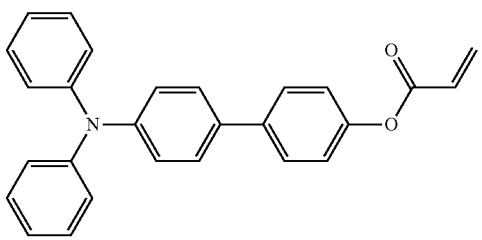
<Exemplary Compound 3-14>
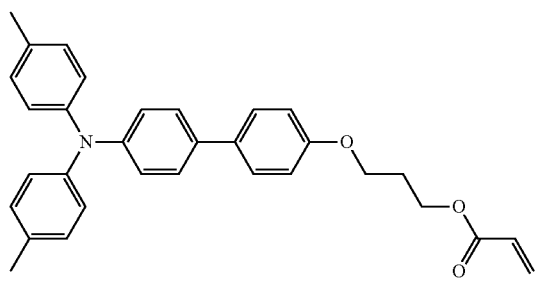
<Exemplary Compound 3-15>
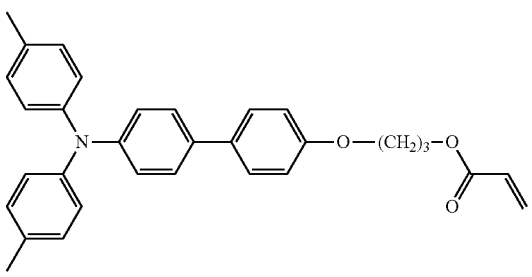
<Exemplary Compound 3-16>
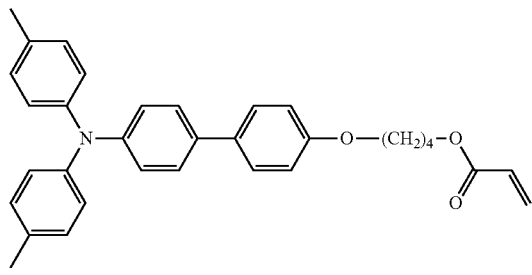
<Exemplary Compound 3-17>
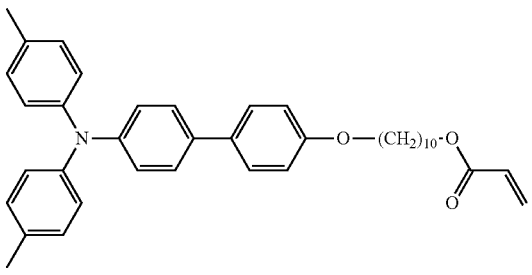
<Exemplary Compound 3-18>
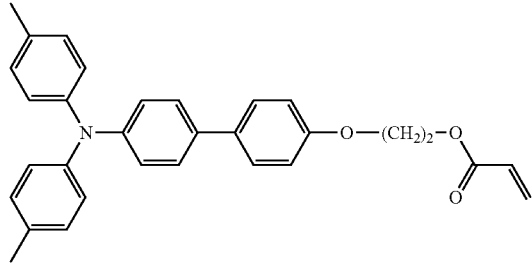
<Exemplary Compound 3-19>
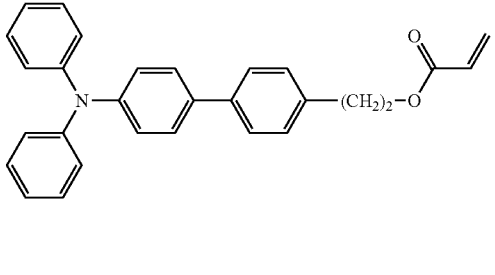

-continued
<Exemplary Compound 3-20>
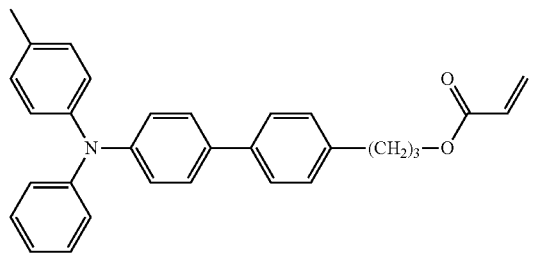
<Exemplary Compound 3-21>
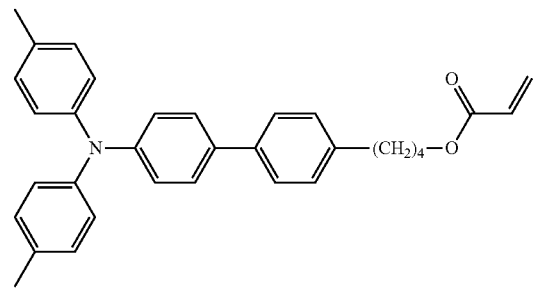
<Exemplary 3-22>
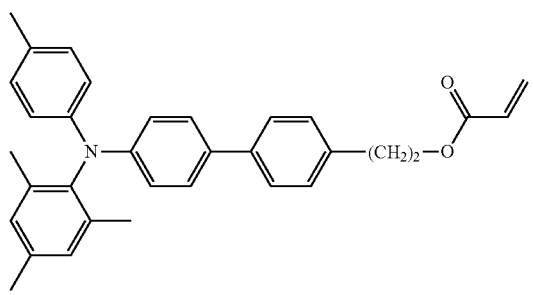
<Exemplary Compound 3-23>
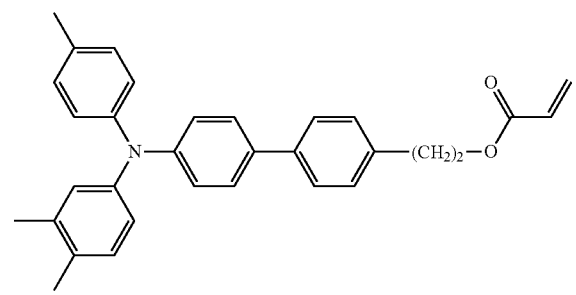
<Exemplary Compound 3-24>
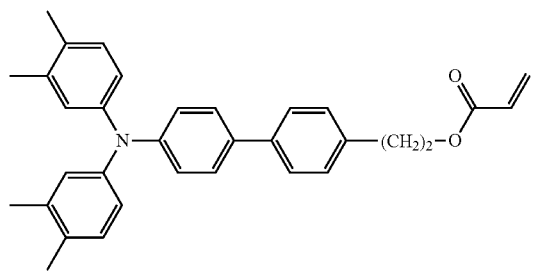
<Exemplary Compound 3-25>
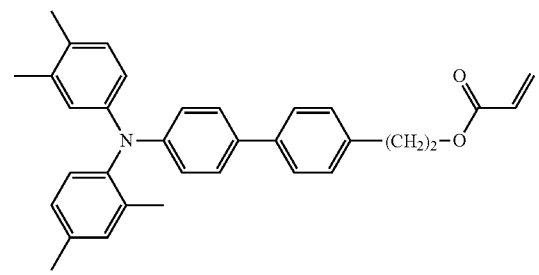
<Exemplary Compound 3-26>
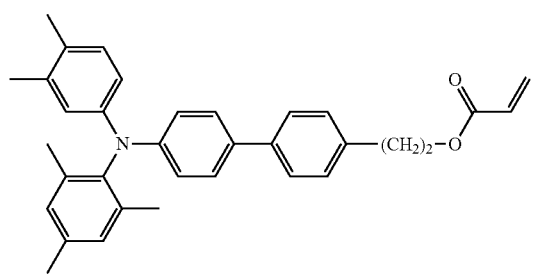
<Exemplary Compound 3-27>
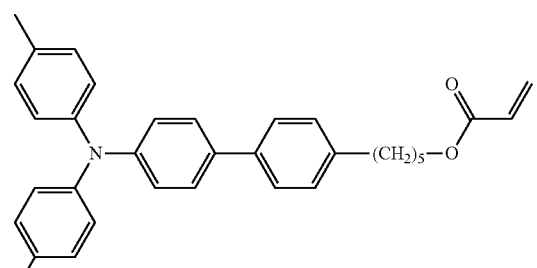
<Exemplary Compound 3-28>
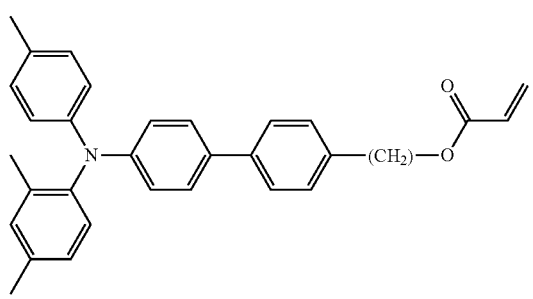
<Exemplary Compound 3-29>
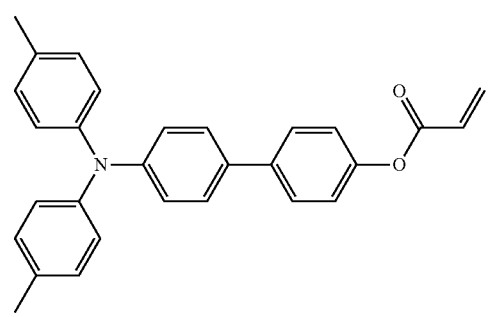

-continued
<Exemplary Compound 3-30>
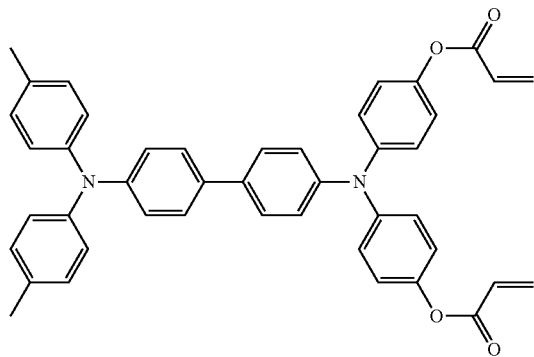
<Exemplary Compound 3-31>
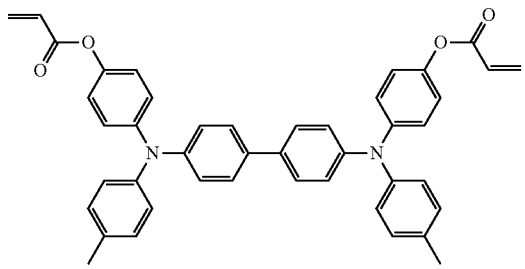
<Exemplary Compound 3-32>
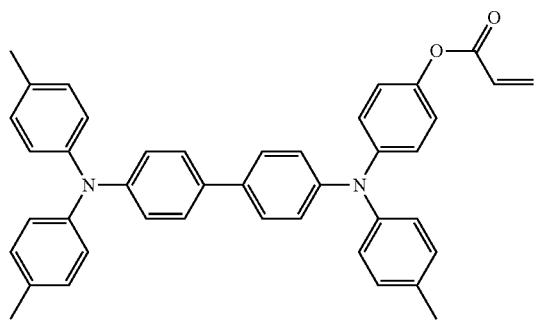
<Exemplary Compound 3-33>
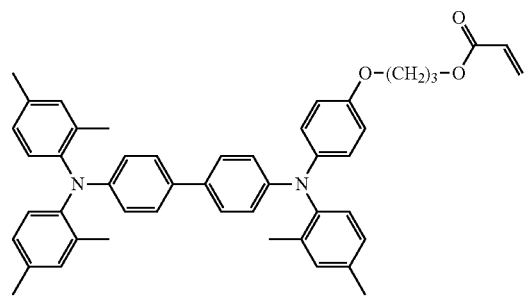
<Exemplary Compound 3-34>
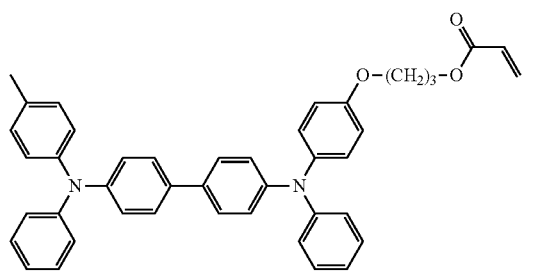
<Exemplary Compound 3-35>
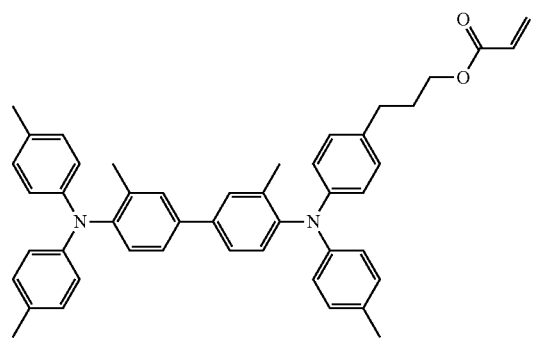
<Exemplary Compound 3-36>
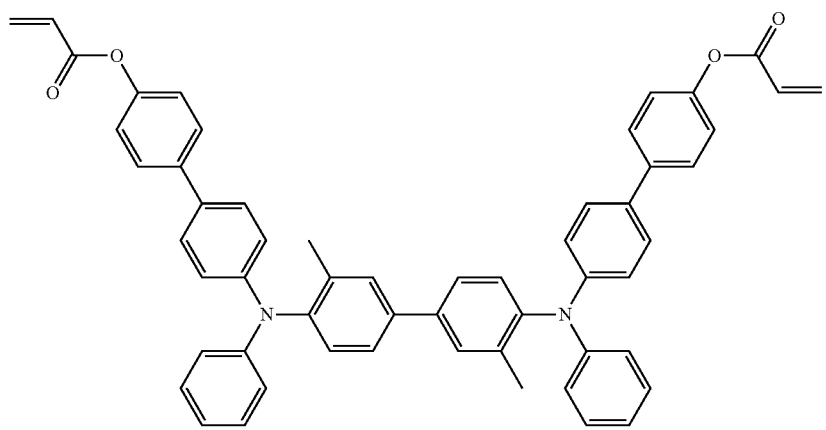

-continued

<Exemplary Compound 3-37>

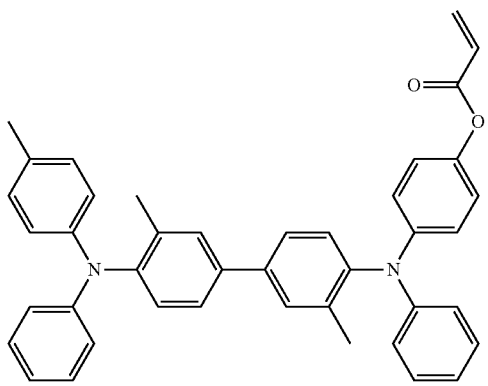

<Exemplary Compound 3-38>

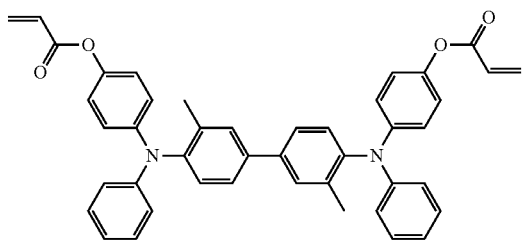

<Exemplary Compound 3-39>

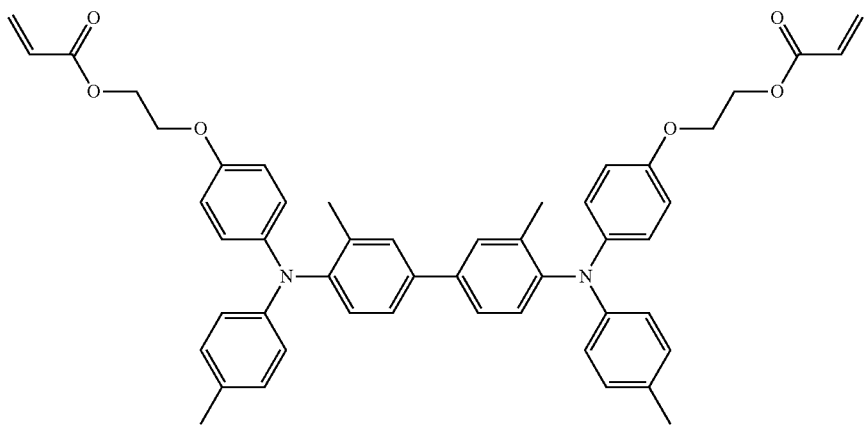

<Exemplary Compound 3-40>

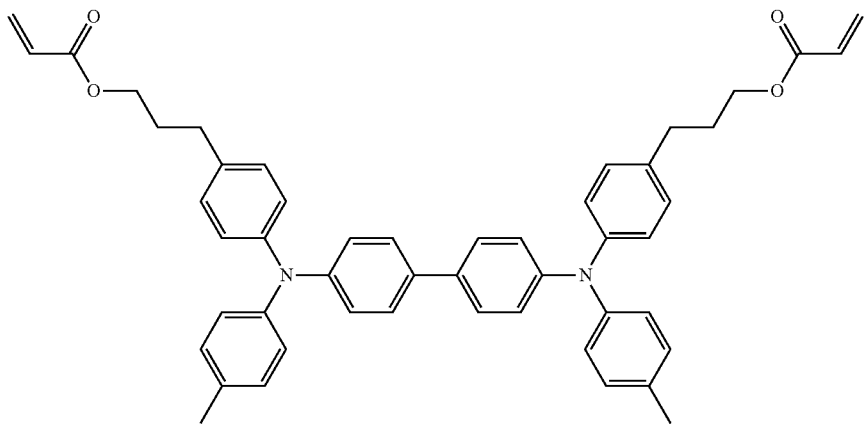

<<Another Polymerizable Compound>>

The polymerizable material for forming the second electrochromic layer may optionally include another polymerizable compound.

The above-mentioned another radical-polymerizable compound is different from the radical-polymerizable compound having a triarylamine skeleton. Moreover, the above-mentioned another radical-polymerizable compound is a compound including at least one radical-polymerizable functional group. Examples of the above-mentioned another radical-polymerizable compound include a monofunctional radical-polymerizable compound, a difunctional radical-polymerizable compound, a trifunctional or higher polyfunctional radical-polymerizable compound, a functional monomer, and a radical-polymerizable oligomer. Among the above-listed examples, a difunctional or higher polyfunctional radical-polymerizable compound is particularly preferable. A radical-polymerizable functional group of the above-mentioned another radical-polymerizable compound is identical to the radical-polymerizable functional group of the radical-polymerizable compound having a triarylamine skeleton. Among the above-listed examples, an acryloyloxy group and a methacryloyloxy group are particularly preferable.

Examples of the monofunctional radical-polymerizable compound include 2-(2-ethoxyethoxy)ethylacrylate, methoxy polyethylene glycol monoacrylate, methoxy polyethylene glycol monomethacrylate, phenoxy polyethylene glycol acrylate, 2-acryloyloxyethylsuccinate, 2-ethylhexylacrylate, 2-hydroxyethylacrylate, 2-hydroxypropylacrylate, tetrahydrofurfurylacrylate, 2-ethylhexylcarbitol acrylate, 3-methoxybutyl acrylate, benzylacrylate, cyclohexyl acrylate, isoamyl acrylate, isobutyl acrylate, methoxy triethylene glycol acrylate, phenoxy tetraethylene glycol acrylate, cetyl acrylate, isostearyl acrylate, stearyl acrylate, and a styrene monomer. The above-listed examples may be used alone or in combination.

Examples of the difunctional radical-polymerizable compound include 1,3-butanediol diacrylate, 1,4-butanediol diacrylate, 1,4-butanediol dimethacrylate, 1,6-hexanediol diacrylate, 1,6-hexanediol dimethacrylate, diethylene glycol diacrylate, polyethylene glycol diacrylate, neopentyl glycol diacrylate, EO-modified bisphenol A diacrylate, EO-modified bisphenol F diacrylate, and neopentyl glycol diacrylate. The above-listed examples may be used alone or in combination.

Examples of the trifunctional or higher radical-polymerizable compound include trimethylolpropane triacrylate (TMPTA), trimethylolpropane trimethacrylate, EO-modified trimethylolpropane triacrylate, PO-modified trimethylolpropane triacrylate, caprolactone-modified trimethylolpropane triacrylate, HPA-modified trimethylolpropane trimethacrylate, pentaerythritol triacrylate, pentaerythritol tetraacrylate (PETTA), glycerol triacrylate, ECH-modified glycerol triacrylate, EO-modified glycerol triacrylate, PO-modified glycerol triacrylate, tris(acryloxyethyl)isocyanurate, dipentaerythritol hexaacrylate (DPHA), caprolactone-modified dipentaerythritol hexaacrylate, dipentaerythritolhydroxy pentaacrylate, alkyl-modified dipentaerythritol pentaacrylate, alkyl-modified dipentaerythritol tetraacrylate, alkyl-modified dipentaerythritol triacrylate, dimethylolpropane tetraacrylate (DTMPTA), pentaerythritol ethoxytetraacrylate, EO-modified phosphoric acid triacrylate, and 2,2,5,5-tetrahydroxymethylcyclopentanone tetraacrylate. The above-listed examples may be used alone or in combination. Note that, the term "EO-modified" above denotes ethylene oxide-modified and the term "PO-modified" above denotes propylene oxide-modified.

Examples of the functional monomer include: monomers substituted with a fluorine atom, such as octafluoropentyl acrylate, 2-perfluorooctylethylacrylate, 2-perfluorooctylethylmethacrylate, and 2-perfluoroisononylethylacrylate; vinyl monomers including a polysiloxane group having from 20 through 70 repeating units of siloxane, such as acryloyl polydimethylsiloxane ethyl, methacryloyl polydimethylsiloxane ethyl, acryloyl polydimethylsiloxane propyl, acryloyl polydimethylsiloxane butyl, and diacryloyl polydimethylsiloxane diethyl, disclosed in Japanese Examined Application Publication Nos. 05-60503 and 06-45770; acrylates; and methacrylate. The above-listed examples may be used alone or in combination.

Examples of the radical-polymerizable oligomer include an epoxy acrylate-based oligomer, a urethane acrylate-based oligomer, and a polyester acrylate-based oligomer.

The radical-polymerizable compound having a triarylamine skeleton, or another radical-polymerizable compound that is different from the radical-polymerizable compound having a triarylamine skeleton, or both preferably have two or more radical-polymerizable functional groups in view of formation of a cross-linked product.

An amount of the radical-polymerizable compound having a triarylamine skeleton is preferably 10% by mass or greater but 100% by mass or less, and more preferably 30% by mass or greater but 90% by mass or less, relative to a total amount of the materials exhibiting an electrochromic function in the polymerizable material. When the amount thereof is 10% by mass or greater, an electrochromic function of the second electrochromic layer can be sufficiently exhibited, durability and coloring sensitivity of a resultant device are excellent against repetitive use with application of voltage. An electrochromic function is exhibited even when the amount thereof is 100% by mass. In this case, coloring density relative a thickness is the highest. In contrast, however, compatibility to ions required for exchanging charges may be low. As a result, deteriorations in electrical properties, such as low durability due to repetitive use with application of voltage, may be caused. Although it cannot be generalized because electrical properties required vary depending on a process for use, the amount thereof is more preferably 30% by mass or greater but 90% by mass or less in view of balance between coloring sensitivity and durability against repetitive use.

<<Polymerization Initiator>>

The polymerizable material may optionally include a polymerization initiator (e.g., a radical polymerization initiator) in order to efficiently proceed a polymerization reaction of the radical-polymerizable compound having a triarylamine skeleton.

Examples of the polymerization initiator include a thermal polymerization initiator and a photopolymerization initiator. In view of polymerization efficiency, the polymerization initiator is preferably a photopolymerization initiator.

The thermal polymerization initiator is not particularly limited and may be appropriately selected depending on the intended purpose. Examples of the thermal polymerization initiator include: a peroxide-based initiator, such as 2,5-dimethylhexane-2,5-dihydroperoxide, dicumyl peroxide, benzoyl peroxide, t-butylcumyl peroxide, 2,5-dimethyl-2,5-di(peroxybenzoyl)hexyne-3, di-t-butylperoxide, t-butylhydroperoxide, cumene hydroperoxide, and lauroyl peroxide; and an azo-based initiator, such as azobisisobutyl nitrile, azobiscyclohexane carbonitrile, methyl azobisisobutyrate, azobisisobutylamidine hydrochloride, and 4,4'-azobis-4-cyanovaleric acid. The above-listed examples may be used alone or in combination.

The photopolymerization initiator is not particularly limited and may be appropriately selected depending on the intended purpose. Examples of the photopolymerization initiator include: an acetophenone-based or ketal-based photopolymerization initiator, such as diethoxyacetophenone, 2,2-dimethoxy-1,2-diphenylethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1, 2-hydroxy-2-methyl-1-phenylpropan-1-one, 2-methyl-2-morpholino(4-methylthiophenyl)propan-1-one, and 1-phenyl-1,2-propanedione-2-(o-ethoxycarbonyl)oxime; benzoin ether-based photopolymerization initiators, such as benzoin, benzoinmethyl ether, benzoinethyl ether, benzoin isobutyl ether, and benzoin isopropyl ether; a benzophenone-based photopolymerization initiator, such as benzophenone, 4-hydroxybenzophenone, methyl o-benzoyl benzoate, 2-benzoylnaphthalene, 4-benzoylbiphenyl, 4-benzoyl phenyl ether, acrylated benzophenone, and 1,4-benzoylbenzene; and a thioxanthone-based photopolymerization initiator, such as 2-isopropylthioxanthone, 2-chlorothioxanthone, 2,4-dimethylthioxanthone, 2,4-diethylthioxanthone, and 2,4-dichlorothioxanthone.

Examples of other photopolymerization initiators include ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxylic acid ester, 9,10-phenanthrene, acridine-based compounds, triazine-based compounds, and imidazole-based compounds. The above-listed examples may be used alone or in combination.

Note that, a compound having an effect of accelerating photopolymerization may be used alone or in combination with the photopolymerizaiton initiator. Examples of such a compound include triethanolamine, methyl diethanol amine, ethyl 4-dimethylaminobenzoate, isoamyl 4-dimethylaminobenzoate, (2-dimethylamino)ethyl benzoate, and 4,4'-dimethylaminobenzophenone.

An amount of the polymerization initiator in the polymerizable material for forming the second electrochromic layer is preferably 0.5 parts by mass or greater but 40 parts by mass or less, and more preferably 1 part by mass or greater but 20 parts by mass or less, relative to 100 parts by mass of a total amount of the radical polymerizable compound(s).

The total amount of the radical-polymerizable compound(s) means a sum of all of the one or more radical-polymerizable compounds included in the polymerizable material.

<Electrolyte Layer>

The electrolyte layer includes at least an electrolyte.

<<Electrolyte>>

The electrolyte is not particularly limited and any of electrolytes known in the art can be used. An anion of the electrolyte is preferably a monovalent anion having an oxidation potential higher than a reduction potential of the dication of General Formula 1 by 3.1 V or greater. Examples of the anion include $(FSO_2)_2N^-$, $(CF_3SO_2)_2N^-$, $(CN)_4B^-$, $BF_4^-$, $CF_3BF_3^-$, $PF_6^-$, $ClO_4^-$, $(C_2F_5SO_2)_2N^-$, $(C_4F_9SO_2)_2N^-$, $CF_3SO_3$, $C_2F_5SO_3$, $C_4F_9SO_3$, $(C_2F_5)_3PF_3^-$, and $(CF_3SO_2)_3C^-$. Use of an electrolyte having any of the above-listed anions can prevent coloring due to a CT transition of the electrochromic compound, when ion exchange between the anion of the electrochromic compound and the anion of the electrolyte occurs inside an electrochromic element. Therefore, an electrochromic element having excellent transparency can be obtained.

The anion of the electrolyte is more preferably $(FSO_2)_2N^-$, $(CF_3SO_2)_2N^-$, $(CN)_4B^-$, $BF_4^-$, $PF_6^-$, or $ClO_4$. Use of an electrolyte having any of the above-listed anions can prevent coloring due to a CT transition of the electrochromic compound, when ion exchange between the anion of the electrochromic compound and the anion of the electrolyte occurs inside an electrochromic element. Moreover, the above-listed anions are stable, and not too large so sufficient response speed can be obtained. Therefore, an electrochromic element having excellent response as well as excellent transparency can be obtained.

A cation of the electrolyte is not particularly limited. Examples of the electrolyte include: metal ion-based electrolytes, such as Li salt, Na salt, K salt, and Mg salt; imidazole derivatives, such as N, N-dimethylimidazole salt, N, N-methylethylimidazole salt, N, N-methylpropylimidazole salt, N, N-methylbutylimidazole salt, and N, N-allylbutylimidazole salt; pyridinium derivatives, such as N,N-dimethylpyridinium salt, and N,N-methylpropylpyridinium salt; pyrrolidinium derivatives, such as N,N-dimethylpyrrolidinium salt, N-ethyl-N-methylpyrrolidinium salt, N-methyl-N-propylpyrrolidinium salt, N-butyl-N-methylpyrrolidinium salt, N-methyl-N-pentylpyrrolidinium salt, and N-hexyl-N-methylpyrrolidinium salt; and aliphatic quaternary ammonium-based electrolytes, such as trimethylpropyl ammonium salt, trimethylhexyl ammonium salt, and triethylhexyl ammonium salt.

The anion and the cation may be used with any combination. The above-listed anions and the above-listed cations may be each used alone or in combination.

Particularly preferred is a combination of the anion and the cation, which a melting point of the electrolyte is room temperature or lower. Specifically, an ionic liquid is preferably used as the electrolyte. Moreover, an organic ionic liquid is preferably used because the organic ionic liquid has a molecular structure, with which the organic ionic liquid is present as a liquid in a wide temperature range including room temperature.

The electrolyte may be directly dissolved in a photopolymerizable monomer, oligomer, or liquid crystal material. When the solubility of the electrolyte is poor, the electrolyte is dissolved in a small amount of a solvent, and the resultant solution may be mixed with the photopolymerizable monomer, oligomer, or liquid crystal material.

Examples of the solvent include propylene carbonate, acetonitrile, γ-butyrolactone, ethylene carbonate, sulfolane, dioxolane, tetrahydrofuran, 2-methyltetrahydrofuran, dimethyl sulfoxide, 1,2-dimethoxyethane, 1,2-ethoxymethoxyethane, polyethylene glycol, alcohols, and mixed solvents thereof.

The electrolyte layer is not necessarily a low viscous liquid. The electrolyte layer may be a gel, crosslinked polymer, or dispersed liquid crystals. When the electrolyte is formed into a gel or a solid, advantages, such as improvement in durability of an element, and improvement in reliability, can be obtained.

It is preferred that the electrolyte be retained in the polymer resin as the solidification method. As a result, high ion conductivity and solid strength can be obtained.

Moreover, the polymer resin is preferably a photocurable resin. Compared to thermal polymerization or formation of a thin film by evaporating a solvent, an element can be produced at a low temperature for a short period of time.

The average thickness of the electrolyte layer including the electrolyte is not particularly limited and may be appropriately selected depending on the intended purpose. The average thickness of the electrolyte layer is preferably 100 nm or greater but 100 μm or less.

The average thickness of the electrolyte layer is not particularly limited and may be appropriately selected depending on the intended purpose. The average thickness of the electrolyte layer is preferably 0.1 times or greater but 1,000 times or less the average thickness of the first electrochromic layer.

<First Electrode and Second Electrode>

A material of the first electrode and a material of the second electrode are not particularly limited. Any of conductors typically used can be used.

A transparent electrode is not particularly limited and may be appropriately selected depending on the intended purpose, as long as a material of the transparent electrode is a transparent material having conductivity. Examples of the transparent material include inorganic materials, such as tin-doped indium oxide (may be referred to as "ITO"), fluorine-doped tin oxide, antimony-doped tin oxide, and zinc oxide.

Among the above-listed examples, InSnO, GaZnO, SnO, $In_2O_3$, and ZnO are preferable.

Moreover, usable is an electrode whose conductivity is improved with maintaining transparency, by forming carbon nanotubes having transparency, or other non-transmittance material having high conductivity (e.g., Au, Ag, Pt, and Cu) into a fine network.

A thickness of each of the first electrode and the second electrode is adjusted to obtain the electrical resistance value with which a redox reaction of the electrochromic layer is carried out.

In the case where ITO is used as a material of the first electrode and a material of the second electrode, a thickness of each of the first electrode and the second electrode is, for example, 50 nm or greater but 500 nm or less.

As a production method of each of the first electrode and the second electrode, vacuum vapor deposition, sputtering, ion plating, etc., can be used.

When a material of each of the first electrode and the second electrode is a material that can be formed through coating, various printing methods, such as spin coating, casting, microgravure coating, gravure coating, bar coating, roll coating, wire bar coating, dip coating, slit coating, capillary coating, spray coating, nozzle coating, gravure printing, screen printing, flexo printing, offset printing, reverse printing, and inkjet printing can be used as the production method.

<Other Members>

The electrochromic element of the present disclosure may include other members according to the necessity.

The above-mentioned other members are not particularly limited and may be appropriately selected depending on the intended purpose. Examples thereof include a support, a sealing material, and a protective layer.

<<Support>>

As the support, any of know organic materials or inorganic materials can be used as it is as long as it is a transparent material that can support other layers disposed thereon.

As the support, for example, a glass substrate, such as non-alkali glass, borosilicate glass, float glass, and soda-lime glass, can be used.

Alternatively, a resin substrate of a polycarbonate resin, an acrylic resin, polyethylene, polyvinyl chloride, polyester, an epoxy resin, a melamine resin, a phenol resin, a polyurethane resin, a polyimide resin, etc. may be used as the support.

Moreover, a surface of the support may be coated with a transparent insulating layer, an UV cut layer, an anti-reflection layer, etc. in order to enhance water vapor barrier properties, gas barrier properties, and visibility.

A shape of the support may be a circle, and the shape thereof is not particularly limited.

As the support, a plurality of supports may be laminated for use. For example, water vapor barrier properties and gas barrier properties can be enhanced by sandwiching the electrochromic element with a pair of glass substrates.

<<Sealing Material>>

The sealing material has a function of sealing side surface of the electrochromic element formed by binding to prevent leakage of the electrolyte, or preventing contamination from unnecessary elements for the electrochromic element to be operated stably, such as moisture or oxygen in the atmosphere. The sealing material is not particularly limited. For example, a UV-curable resin or a heat-curable resin may be used as the sealing material. Specific examples thereof include an acryl-based resin, a urethane-based resin, and an epoxy-based resin.

<<Protective Layer>>

A role of the protective layer is to protect the element from external stress or chemicals used during a washing process, to prevent leakage of the electrolyte, or to prevent entry of elements unnecessary for the electrochromic element to be operated stably, such as moisture or oxygen in the atmosphere.

A thickness of the protective layer is not particularly limited and may be appropriately selected depending on the intended purpose. The thickness of the protective layer is preferably 1 μm or greater but 200 μm or less.

As a material of the protective layer, for example, a UV-curable resin, or a heat-curable resin may be used. Examples thereof include an acryl-based resin, a urethane-based resin, and an epoxy-based resin.

< Use>

Since the electrochromic element of the present disclosure has excellent transparency, the electrochromic element can be suitably used, for example, for electrochromic displays, large-scale display panels (e.g., a display panel for displaying stock and share prices), anti-glare mirrors, light-adjusting elements (e.g., light-adjusting glass, a light-adjusting lens, and a light-adjusting film), low-voltage-driven elements (e.g., a touch panel key switches), photoswitches, photomemories, electric paper, and electric album.

EXAMPLES

The present disclosure will be described below by way of Examples. The present disclosure should not be construed as being limited to these Examples.

<Measurement of Reduction Potential of Dication>

Octyl viologen dibromide (TOKYO CHEMICAL INDUSTRY CO., LTD.) was dissolved in propylene carbonate so that the amount of the octyl viologen dibromide was to be 0.01 mol/L. In the resultant solution, 1-ethyl-3-methyl-imidazolium bis(fluorosulfonyl)imide (EMIMFSI, available from KANTO CHEMICAL CO., INC.) serving as an electrolyte was dissolved so that the amount thereof was to be 0.1 mol/L to thereby prepare a measuring solution. A glassy carbon electrode was used as a reference electrode, a platinum electrode was used as a counter electrode, and an Ag/Ag+ electrode divided by ion-permeating glass was used as a reference electrode. Cyclic voltammetry was performed using a potentiostat to measure reduction potential of the dication of octyl viologen. Note that, the dication of Exemplary Compounds 1-1 to 1-18 and 1-24 to 1-26 all having a common viologen skeleton had the same reduction potential.

Moreover, each of Exemplary Compounds 1-19 to 1-23 was dissolved in propylene carbonate so that the amount thereof was to be 0.01 mol/L, and reduction potential of dication was measured in the same manner as described above. As a result, the reduction potentials thereof were lower than the reduction potential of the dication of octyl viologen.

<Measurement of Oxidation Potential of Anion>

Subsequently, 1-ethyl-3-methyl-imidazolium bis(fluorosulfonyl)imide as an anion of each of Exemplary Compounds 1-1 and 1-7 was dissolved in propylene carbonate so that the amount thereof was to be 0.1 mol/L. The potential was swept to the side of oxidation to measure oxidation potential of the FSI anion. As a result, any significant reaction current was not observed at the potential higher than the reduction potential of the dication of the octyl viologen by 3.1 V. Specifically, the oxidation potential of the bis(fluorosulfonyl)imide anion was higher than the reduction potential of the dication of Exemplary Compounds 1-1 to 1-26 by 3.1 V or greater.

Similarly, 1-ethyl-3-methyl-imidazolium bis(trifluoromethanesulfonyl)imide was an anion of Exemplary Compounds 1-2, and 1-8 to 1-34, 1-ethyl-3-methyl-imidazolium tetracyanoborate was used as an anion of Exemplary Compound 1-3, 1-ethyl-3-methyl-imidazolium tetrafluoroborate was used as Exemplary Compound 1-4, 1-butyl-3-methyl-imidazolium hexafluorophosphate was used as an anion of Exemplary Compound 1-5, and tetrabutylammonium perchloride was used as an anion of Exemplary Compound 1-6. Each of the anions was dissolved in propyl carbonate so that the amount thereof was to be 0.1 mol/L, and the potential was swept to the side of oxidation to measure oxidation potential of each anion.

As a result, any significant reaction current was not observed at the potential higher than the reduction potential of the dication of octyl viologen by 3.1 V. In any of the measurements, oxidation current started flowing at around the potential high than the reduction potential of the dication of octylviologen by greater than 3.1 V, and it was implausible that all of the anions had the same oxidation potential. Therefore, the current was assumed to be current due to oxidation of propylene carbonate. Therefore, specific oxidation potential of each of anions was unclear, but it was undoubtedly higher than the reduction potential of the dication of octyl viologen by 3.1 V or greater. Specifically, it was found that oxidation potential of these anions was higher than reduction potential of the dication of Exemplary Compounds 1-1 to 1-26 by 3.1 V or greater.

Example 1

<Production of Electrochromic Layer>

A titanium oxide nanoparticle dispersion liquid (product name: SP210, available from Showa Titanium Co., Ltd., average particle diameter: about 20 nm) was applied on an ITO glass substrate (40 mm×40 mm, thickness: 0.7 mm, ITO film thickness: about 100 nm) serving as a first electrode by spin coating, and the dispersion liquid was subjected to annealing for 15 minutes at 120° C., to thereby form a nano-structure semiconductor material formed of a titanium oxide particle film having a thickness of 2.5 μm.

Onto the titanium oxide particle film, a coating liquid that was a mmol % 2,2,3,3-tetrafluoropropanol solution of Exemplary Compound 1-1 was applied by spin coating, and the coating liquid was subjected to annealing for 10 minutes at 120° C., to thereby form a first electrochromic layer having a thickness of 2.5 μm on the first electrode, where the electrochromic layer included the titanium oxide particles on surfaces of which Exemplary Compound 1-1 was deposited.

<Production of Second Electrochromic Layer>

A solution obtained by mixing Exemplary Compound 3-10 having a triarylamine skeleton and Exemplary Compound 3-40 having a tetraarylbenzidine skeleton serving as second electrochromic compounds, BLEMMER AME400 (available from NOF CORPORATION) and BLEMMER ADE400A (available from NOF CORPORATION) serving as other polymerizable compounds, Irgacure184 serving as a polymerization initiator, and 2-butanone serving as a solvent at a mass ratio of (Exemplary Compound 3-10: Exemplary Compound 3-40: AME400: ADE400A: Irgacure184: 2-butanone=3:7:6:4:0.1:80) was applied onto an ITO glass substrate (40 mm×40 mm, thickness: 0.7 mm, ITO film thickness: about 100 nm) serving as a second electrode by spin coating, followed by drying. The applied solution was then UV cured in a nitrogen atmosphere, to thereby form a second electrochromic layer having a thickness of 1.3 μm on the second electrochromic electrode.

<Filling with Electrolyte>

First, 195 part by mass of BLEMMER AME400 (available from NOF CORPORATION), 195 parts by mass of BLEMMER ADE400A (available from NOF CORPORATION), 10 parts by mass of IRGACURE184 (available from BASF) serving as a polymerization initiator, and 60 parts by mass of 1-ethyl-3-methyl-imidazolium bis(fluorosulfonyl) imide (EMIMFSI, available from KANTO CHEMICAL CO., INC.) as an electrolyte were mixed as a monomer composition liquid to thereby obtain an electrolyte solution.

The obtained electrolyte solution was weighed and collected using a micropipette by 50 μL, and was dripped on the ITO glass substrate having the first electrochromic layer. The ITO glass substrate having the second electrochromic layer was bonded thereon in a manner that areas for extracting electrodes were secured, to thereby obtain a bonded element.

The obtained bonded element was irradiated with UV for 60 seconds at 10 mW by means of a UV (wavelength: 250 nm) irradiation device (SPOT CURE, available from USHIO INC.). In the manner as described above, an electrochromic element was produced.

The average thickness of the electrolyte layer was 30 μm.

<Evaluation of Colorless Transparency>

The transmittance of the produced electrochromic element was measured by USB4000 available from Ocean Optics. Based on the obtained spectrum, a yellow index (YI) was calculated.

The calculation result is presented in Table 1-1.

<Evaluation of Coloring Density>

The transmittance of the produced electrochromic element at 610 nm was measured by USB4000 available from Ocean Optics, when charge of 10 mC/cm$^2$ was applied par unit area of the coloring area. The measurement result is presented in Table 1-1.

<Evaluation of Durability>

A durability test of the produced electrochromic element was performed for 50 hours at an environmental temperature of 28° C. at a light dose of 250 W/m$^2$ in a weatherometer SUNTEST CPS+(available from Tokyo Seiki Seisaku-sho, Ltd.) in a state where the electrochromic element was colored by applying a charge of 5 mC/cm$^2$ per unit area of the coloring area. After the test, the device was bleached. Then, transmittance was measured by means of USB4000 available from Ocean Optics and a yellow index (YI) was calculated from the obtained spectrum. ΔYI, which was a value indicating an increased amount of YI from the value thereof before the durability test, was calculated. Note that, the calculation of the yellow index value was performed in the same manner as in the calculation performed in the evaluation of colorless transparency.

The calculation result is presented in Table 1-1.

Examples 2 to 90

Electrochromic elements were produced and evaluated in the same manner as in Example 1, except that the electrochromic compound and/or the electrolyte was changed as presented in Tables 1-1 to 1-4. The results are presented in Tables 1-1 to 1-4. Note that, the abbreviations of the electrolyte are summarized in Table 2.

Comparative Examples 1 to 3

Electrochromic elements were each produced and evaluated in the same manner as in Example 1, except that the electrochromic compound and or the electrolyte was changed as presented in Table 1-4. The electrochromic compounds used for Comparative Examples were the following compounds.

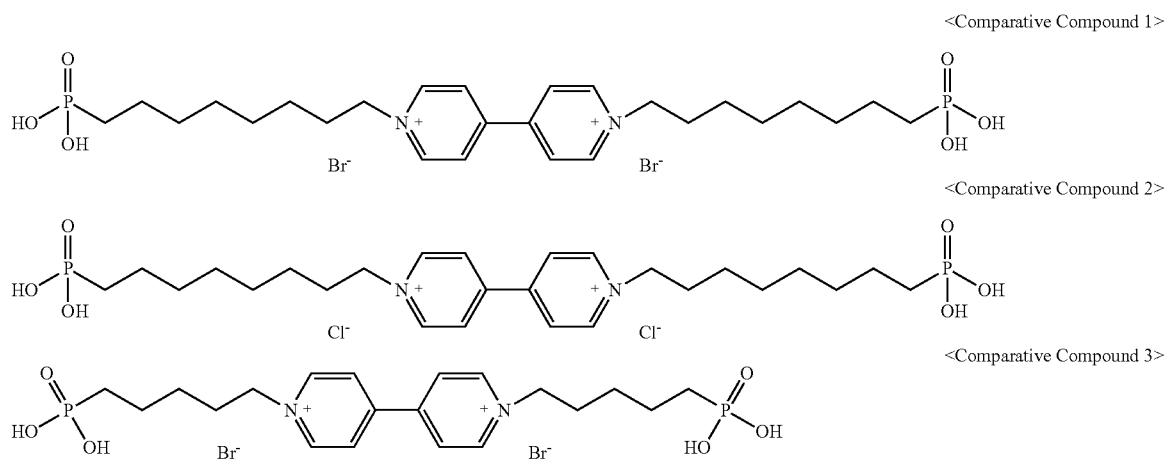

<Comparative Compound 1>

<Comparative Compound 2>

<Comparative Compound 3>

<Measurement of Oxidation Potential of Anion of Comparative Examples>

In the same manner as the measuring method of the oxidation potential of the anion of each of the electrochromic compounds of the present disclosure, an oxidation potential of the 1-ethyl-3-methyl-imidazolium bromide as an anion of Comparative Compounds 1 and 3, and an oxidation potential of the 1-ethyl-3-methyl-imidazolium chloride as an anion of Comparative Compound 2 were measured. As a result, the current due to an oxidation reaction was confirmed with 1-ethyl-3-methyl-imidazolium bromide at the potential higher than the reduction potential of the dication of octyl viologen by 1.1 V, and the current due to an oxidation reaction was confirmed with 1-ethyl-3-methyl-imidazolium chloride at the potential higher than the reduction potential of viologen by 1.4 V. Specifically, it was found that oxidation potential of each of the anions was not higher than the reduction potential of each of the dications of Comparative Compounds 1 to 3 by 3.1 V or greater.

TABLE 1-1

| | First electrochromic compound | Second electrochromic compound | | Electrolyte | Transparency YI | Coloring density T at 610 nm | Durability ΔYI |
|---|---|---|---|---|---|---|---|
| | | triarylamine Exemplary Compound No. | tetraaryl bendizine Exemplary Compound No. | | | | |
| Ex. 1 | Exemplary Compound 1-1 | 3-10 | 3-40 | EMIMFSI | 1.1 | 7.10 | 11.1 |
| Ex. 2 | Exemplary Compound 1-2 | 3-10 | 3-40 | EMIMFSI | 0.6 | 5.07 | 10.3 |
| Ex. 3 | Exemplary Compound 1-3 | 3-10 | 3-40 | EMIMFSI | 1.0 | 7.19 | 13.1 |
| Ex. 4 | Exemplary Compound 1-4 | 3-10 | 3-40 | EMIMFSI | 0.8 | 6.62 | 13.7 |
| Ex. 5 | Exemplary Compound 1-5 | 3-10 | 3-40 | EMIMFSI | 2.3 | 7.38 | 13.5 |
| Ex. 6 | Exemplary Compound 1-6 | 3-10 | 3-40 | EMIMFSI | 3.1 | 7.45 | 13.6 |
| Ex. 7 | Exemplary Compound 1-7 | 3-10 | 3-40 | EMIMFSI | 1.3 | 6.89 | 11.1 |
| Ex. 8 | Exemplary Compound 1-8 | 3-10 | 3-40 | EMIMFSI | 0.6 | 4.99 | 10.8 |
| Ex. 9 | Exemplary Compound 1-1 | 3-10 | 3-40 | EMIMTFSI | 1.6 | 7.06 | 10.4 |
| Ex. 10 | Exemplary Compound 1-2 | 3-10 | 3-40 | EMIMTFSI | 0.8 | 5.17 | 10.5 |
| Ex. 11 | Exemplary Compound 1-3 | 3-10 | 3-40 | EMIMTFSI | 1.4 | 7.31 | 13.6 |
| Ex. 12 | Exemplary Compound 1-4 | 3-10 | 3-40 | EMIMTFSI | 1.0 | 6.49 | 13.1 |
| Ex. 13 | Exemplary Compound 1-5 | 3-10 | 3-40 | EMIMTFSI | 2.0 | 7.16 | 12.8 |
| Ex. 14 | Exemplary Compound 1-6 | 3-10 | 3-40 | EMIMTFSI | 2.3 | 7.55 | 13.6 |
| Ex. 15 | Exemplary Compound 1-7 | 3-10 | 3-40 | EMIMTFSI | 1.4 | 6.92 | 11.6 |
| Ex. 16 | Exemplary Compound 1-8 | 3-10 | 3-40 | EMIMTFSI | 0.7 | 4.98 | 10.7 |
| Ex. 17 | Exemplary Compound 1-1 | 3-10 | 3-40 | EMIMBF4 | 1.1 | 7.16 | 11.1 |

TABLE 1-1-continued

|  | First electrochromic compound | Second electrochromic compound | | Electrolyte | Transparency YI | Coloring density T at 610 nm | Durability ΔYI |
|---|---|---|---|---|---|---|---|
|  |  | triarylamine Exemplary Compound No. | tetraaryl bendizine Exemplary Compound No. |  |  |  |  |
| Ex. 18 | Exemplary Compound 1-2 | 3-10 | 3-40 | EMIMBF4 | 0.7 | 5.10 | 11.1 |
| Ex. 19 | Exemplary Compound 1-1 | 3-10 | 3-40 | BMIMPF6 | 1.6 | 7.01 | 11.1 |
| Ex. 20 | Exemplary Compound 1-2 | 3-10 | 3-40 | BMIMPF6 | 0.6 | 5.04 | 10.6 |
| Ex. 21 | Exemplary Compound 1-1 | 3-10 | 3-40 | EMIMTCB | 1.7 | 7.06 | 11.8 |
| Ex. 22 | Exemplary Compound 1-2 | 3-10 | 3-40 | EMIMTCB | 1.2 | 5.01 | 10.7 |
| Ex. 23 | Exemplary Compound 1-1 | 3-10 | 3-40 | TBAP + PC | 2.0 | 7.49 | 11.5 |
| Ex. 24 | Exemplary Compound 1-2 | 3-10 | 3-40 | TBAP + PC | 1.3 | 5.36 | 10.3 |
| Ex. 25 | Exemplary Compound 1-2 | 3-1 | 3-40 | EMIMTFSI | 0.8 | 5.21 | 10.7 |

TABLE 1-2

|  | First electrochromic compound | Second electrochromic compound | | Electrolyte | Transparency YI | Coloring density T at 610 nm | Durability ΔYI |
|---|---|---|---|---|---|---|---|
|  |  | triarylamine Exemplary Compound No. | tetraaryl bendizine Exemplary Compound No. |  |  |  |  |
| Ex. 26 | Exemplary Compound 1-2 | 3-2 | 3-40 | EMIMTFSI | 0.8 | 5.17 | 10.8 |
| Ex. 27 | Exemplary Compound 1-2 | 3-3 | 3-40 | EMIMTFSI | 0.7 | 5.09 | 10.4 |
| Ex. 28 | Exemplary Compound 1-2 | 3-4 | 3-40 | EMIMTFSI | 0.8 | 5.21 | 10.2 |
| Ex. 29 | Exemplary Compound 1-2 | 3-5 | 3-40 | EMIMTFSI | 0.6 | 5.03 | 10.9 |
| Ex. 30 | Exemplary Compound 1-2 | 3-6 | 3-40 | EMIMTFSI | 0.9 | 5.07 | 10.2 |
| Ex. 31 | Exemplary Compound 1-2 | 3-7 | 3-40 | EMIMTFSI | 0.7 | 5.06 | 10.5 |
| Ex. 32 | Exemplary Compound 1-2 | 3-8 | 3-40 | EMIMTFSI | 0.8 | 5.21 | 10.1 |
| Ex. 33 | Exemplary Compound 1-2 | 3-9 | 3-40 | EMIMTFSI | 0.8 | 5.11 | 10.6 |
| Ex. 34 | Exemplary Compound 1-2 | 3-11 | 3-40 | EMIMTFSI | 0.7 | 5.17 | 10.3 |
| Ex. 35 | Exemplary Compound 1-2 | 3-12 | 3-40 | EMIMTFSI | 0.9 | 5.13 | 10.4 |
| Ex. 36 | Exemplary Compound 1-2 | 3-13 | 3-40 | EMIMTFSI | 0.8 | 5.04 | 10.8 |
| Ex. 37 | Exemplary Compound 1-2 | 3-14 | 3-40 | EMIMTFSI | 0.8 | 5.19 | 10.4 |
| Ex. 38 | Exemplary Compound 1-2 | 3-15 | 3-40 | EMIMTFSI | 1.0 | 5.13 | 10.6 |
| Ex. 39 | Exemplary Compound 1-2 | 3-16 | 3-40 | EMIMTFSI | 0.6 | 5.19 | 10.3 |
| Ex. 40 | Exemplary Compound 1-2 | 3-17 | 3-40 | EMIMTFSI | 0.8 | 5.04 | 10.4 |
| Ex. 41 | Exemplary Compound 1-2 | 3-18 | 3-40 | EMIMTFSI | 0.8 | 5.03 | 10.3 |
| Ex. 42 | Exemplary Compound 1-2 | 3-19 | 3-40 | EMIMTFSI | 0.7 | 5.08 | 10.8 |
| Ex. 43 | Exemplary Compound 1-2 | 3-20 | 3-40 | EMIMTFSI | 0.7 | 5.11 | 10.7 |
| Ex. 44 | Exemplary Compound 1-2 | 3-21 | 3-40 | EMIMTFSI | 0.7 | 5.16 | 10.5 |
| Ex. 45 | Exemplary Compound 1-2 | 3-22 | 3-40 | EMIMTFSI | 0.8 | 5.08 | 10.6 |
| Ex. 46 | Exemplary Compound 1-2 | 3-23 | 3-40 | EMIMTFSI | 0.8 | 5.13 | 10.4 |
| Ex. 47 | Exemplary Compound 1-2 | 3-24 | 3-40 | EMIMTFSI | 0.8 | 5.12 | 10.8 |

TABLE 1-2-continued

| | First electrochromic compound | Second electrochromic compound | | Electrolyte | Transparency YI | Coloring density T at 610 nm | Durability ΔYI |
|---|---|---|---|---|---|---|---|
| | | triarylamine Exemplary Compound No. | tetraaryl bendizine Exemplary Compound No. | | | | |
| Ex. 48 | Exemplary Compound 1-2 | 3-25 | 3-40 | EMIMTFSI | 0.7 | 5.05 | 10.3 |
| Ex. 49 | Exemplary Compound 1-2 | 3-26 | 3-40 | EMIMTFSI | 0.8 | 5.11 | 10.7 |
| Ex. 50 | Exemplary Compound 1-2 | 3-27 | 3-40 | EMIMTFSI | 0.9 | 5.08 | 10.4 |

TABLE 1-3

| | First electrochromic compound | Second electrochromic compound | | Supporting electrolyte | Transparency YI | Coloring density T at 610 nm | Durability ΔYI |
|---|---|---|---|---|---|---|---|
| | | triarylamine Exemplary Compound No. | tetraaryl bendizine Exemplary Compound No. | | | | |
| Ex. 51 | Exemplary Compound 1-2 | 3-28 | 3-40 | EMIMTFSI | 0.7 | 5.03 | 10.1 |
| Ex. 52 | Exemplary Compound 1-2 | 3-29 | 3-40 | EMIMTFSI | 0.8 | 5.05 | 10.3 |
| Ex. 53 | Exemplary Compound 1-2 | 3-9 | 3-30 | EMIMTFSI | 0.8 | 5.17 | 10.8 |
| Ex. 54 | Exemplary Compound 1-2 | 3-9 | 3-31 | EMIMTFSI | 0.8 | 5.11 | 10.3 |
| Ex. 55 | Exemplary Compound 1-2 | 3-9 | 3-32 | EMIMTFSI | 0.8 | 5.16 | 10.9 |
| Ex. 56 | Exemplary Compound 1-2 | 3-9 | 3-33 | EMIMTFSI | 0.7 | 5.18 | 10.4 |
| Ex. 57 | Exemplary Compound 1-2 | 3-9 | 3-34 | EMIMTFSI | 1 | 5.09 | 10.7 |
| Ex. 58 | Exemplary Compound 1-2 | 3-9 | 3-35 | EMIMTFSI | 1.1 | 5.1 | 10.3 |
| Ex. 59 | Exemplary Compound 1-2 | 3-9 | 3-36 | EMIMTFSI | 1.3 | 5.15 | 11.8 |
| Ex. 60 | Exemplary Compound 1-2 | 3-9 | 3-37 | EMIMTFSI | 1.1 | 5.12 | 11 |
| Ex. 61 | Exemplary Compound 1-2 | 3-9 | 3-38 | EMIMTFSI | 1.4 | 5.17 | 11.1 |
| Ex. 62 | Exemplary Compound 1-2 | 3-9 | 3-39 | EMIMTFSI | 1.2 | 5.19 | 11.2 |
| Ex. 63 | Exemplary Compound 1-2 | 3-10 | 3-30 | EMIMTFSI | 1.3 | 5.13 | 10.5 |
| Ex. 64 | Exemplary Compound 1-2 | 3-10 | 3-31 | EMIMTFSI | 1.5 | 5.14 | 10.7 |
| Ex. 65 | Exemplary Compound 1-2 | 3-10 | 3-32 | EMIMTFSI | 1.6 | 5.13 | 11.5 |
| Ex. 66 | Exemplary Compound 1-2 | 3-10 | 3-33 | EMIMTFSI | 1.1 | 5.12 | 11.3 |
| Ex. 67 | Exemplary Compound 1-2 | 3-10 | 3-34 | EMIMTFSI | 1.1 | 5.15 | 11.4 |
| Ex. 68 | Exemplary Compound 1-2 | 3-10 | 3-35 | EMIMTFSI | 1.4 | 5.16 | 11.4 |
| Ex. 69 | Exemplary Compound 1-2 | 3-10 | 3-36 | EMIMTFSI | 1.3 | 5.14 | 11.3 |
| Ex. 70 | Exemplary Compound 1-2 | 3-10 | 3-37 | EMIMTFSI | 1.3 | 5.13 | 10.6 |
| Ex. 71 | Exemplary Compound 1-2 | 3-10 | 3-38 | EMIMTFSI | 1.4 | 5.17 | 10.8 |
| Ex. 72 | Exemplary Compound 1-2 | 3-10 | 3-39 | EMIMTFSI | 1.3 | 5.18 | 11.4 |
| Ex. 73 | Exemplary Compound 1-9 | 3-10 | 3-39 | EMIMTFSI | 0.6 | 5.14 | 10.4 |
| Ex. 74 | Exemplary Compound 1-10 | 3-10 | 3-39 | EMIMTFSI | 0.7 | 5.12 | 10.8 |
| Ex. 75 | Exemplary Compound 1-11 | 3-10 | 3-39 | EMIMTFSI | 0.6 | 5.07 | 10.5 |

TABLE 1-4

| | | Second electrochromic compound | | | | | |
|---|---|---|---|---|---|---|---|
| | First electrochromic compound | triarylamine Exemplary Compound No. | tetraaryl bendizine Exemplary Compound No. | Supporting electrolyte | Transparency YI | Coloring density T at 610 nm | Durability ΔYI |
| Ex. 76 | Exemplary Compound 1-12 | 3-10 | 3-39 | EMIMTFSI | 0.6 | 5.03 | 9.1 |
| Ex. 77 | Exemplary Compound 1-13 | 3-10 | 3-39 | EMIMTFSI | 0.5 | 5.38 | 9.4 |
| Ex. 78 | Exemplary Compound 1-14 | 3-10 | 3-39 | EMIMTFSI | 0.7 | 4.91 | 10.3 |
| Ex. 79 | Exemplary Compound 1-15 | 3-10 | 3-39 | EMIMTFSI | 0.6 | 4.96 | 9.7 |
| Ex. 80 | Exemplary Compound 1-16 | 3-10 | 3-39 | EMIMTFSI | 0.5 | 4.95 | 10.6 |
| Ex. 81 | Exemplary Compound 1-17 | 3-10 | 3-39 | EMIMTFSI | 0.5 | 4.73 | 10.1 |
| Ex. 82 | Exemplary Compound 1-18 | 3-10 | 3-39 | EMIMTFSI | 0.5 | 4.75 | 9.8 |
| Ex. 83 | Exemplary Compound 1-19 | 3-10 | 3-39 | EMIMTFSI | 0.6 | 7.43 | 11.8 |
| Ex. 84 | Exemplary Compound 1-20 | 3-10 | 3-39 | EMIMTFSI | 0.6 | 7.18 | 11.1 |
| Ex. 85 | Exemplary Compound 1-21 | 3-10 | 3-39 | EMIMTFSI | 0.7 | 8.61 | 12.5 |
| Ex. 86 | Exemplary Compound 1-22 | 3-10 | 3-39 | EMIMTFSI | 0.7 | 5.43 | 12.1 |
| Ex. 87 | Exemplary Compound 1-23 | 3-10 | 3-39 | EMIMTFSI | 0.7 | 9.52 | 12.7 |
| Ex. 88 | Exemplary Compound 1-24 | 3-10 | 3-39 | EMIMTFSI | 0.6 | 5.11 | 10.8 |
| Ex. 89 | Exemplary Compound 1-25 | 3-10 | 3-39 | EMIMTFSI | 0.6 | 5.62 | 11 |
| Ex. 90 | Exemplary Compound 1-26 | 3-10 | 3-39 | EMIMTFSI | 0.6 | 5.22 | 10.7 |
| Comp. Ex. 1 | Comparative Compound 1 | 3-10 | 3-40 | EMIMTFSI | 6.5 | 7.57 | 18.7 |
| Comp. Ex. 2 | Comparative Compound 2 | 3-10 | 3-40 | EMIMTFSI | 4.8 | 7.69 | 16.4 |
| Comp. Ex. 3 | Comparative Compound 3 | 3-10 | 3-40 | EMIMTFSI | 5.8 | 7.43 | 17.1 |

TABLE 2

| | |
|---|---|
| EMIMFSI | 1-ethyl-3-methyl-imidazolium bis(fluorosulfonyl)imide |
| EMIMTFSI | 1-ethyl-3-methyl-imidazolium bis(trifluoromethanesulfonyl)imide |
| EMIMBF4 | 1-ethyl-3-methyl-imidazolium Tetrafluoroborate |
| BMIMPF6 | 1-butyl-3-methyl-imidazolium Hexafluorophosphate |
| EMIMTCB | 1-ethyl-3-methyl-imidazolium Tetracyanoborate |
| TBAP + PC | tetrabutylammonium perchlorate (dissolved in propylene carbonate in the amount of 1 mmol/L in use) |

As a result, it was confirmed that the electrochromic element of the present disclosure had excellent transparency, coloring density, and durability.

For example, embodiments of the present disclosure are as follows.

<1> An electrochromic element including:

a first electrode;

a second electrode disposed to face the first electrode with a gap between the first electrode and the second electrode;

a first electrochromic layer disposed on or above the first electrode, where the first electrochromic layer includes conductor or semiconductor nano-structures and an electrochromic compound; and an electrolyte layer including an electrolyte, disposed between the first electrochromic layer and the second electrode, wherein the electrochromic compound is a compound represented by General Formula 1, and an anion of the electrolyte is a monovalent anion having an oxidation potential higher than a reduction potential of a dication of General Formula 1 by 3.1 V or greater, $$R_1-R_3-W^{2+}\underset{2X^-}{}-\left(Z-W^{2+}\underset{2X^-}{}\right)_k-R_4-R_2 \quad \text{[General Formula 1]}$$

where, in General Formula 1, $R_1$ and $R_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, or a functional group that can bond to a hydroxyl group; $R_3$ and $R_4$ are each an alkylene group having from 1 through 10 carbon atoms or an arylene group that may have a substituent and has 12 or less carbon atoms; Z is alkylene, cycloalkylene, or a divalent group represented by $—R_7—Y—R_8$ (where $R_7$ and $R_8$ are each independently a single bond, alkylene, or cycloalkylene, and Y is arylene, cycloalkylene, heteroarylene, arylene-arylene, or arylene- CR'R"-arylene, where R' and R" form a carbon ring group together with a carbon atom to which R' and R" are bonded), where the alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl; k is 0 or 1; X⁻ is a monovalent anion having an oxidation potential higher than a reduction potential of the dication of General Formula 1 by 3.1 V or greater; and $W^{2+}$ is the dication represented by General Formula 2,

[General Formula 2]

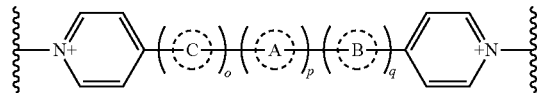

where, in General Formula 2, o, p, and q are each independently 0 or 1; and A, B, and C are each independently an arylene group that may have a substituent and has from 2 through 20 carbon atoms, or a heterocycle group.

<2> The electrochromic element according to <1>, wherein the first electrochromic layer is a first electrochromic layer, in which the electrochromic compound is deposited on the nano-structures.

<3> An electrochromic element including:
a first electrode;
a second electrode disposed to face the first electrode with a gap between the first electrode and the second electrode;
a first electrochromic layer in which an electrochromic compound is deposited on conductor or semiconductor nano-structures, where the first electrochromic layer is disposed on or above the first electrode; and
an electrolyte layer disposed between the first electrochromic layer and the second electrode,
wherein the electrochromic compound is a compound represented by General Formula 1,

[General Formula 1]

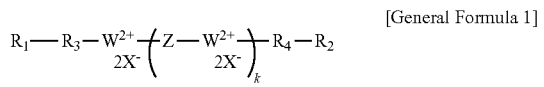

where, in General Formula 1, $R_1$ and $R_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having or less carbon atoms, or a functional group that can bond to a hydroxyl group; $R_3$ and $R_4$ are each an alkylene group having from 1 through 10 carbon atoms or an arylene group that may have a substituent and has 12 or less carbon atoms; Z is alkylene, cycloalkylene, or a divalent group represented by —$R_7$—Y—$R_8$ (where $R_7$ and $R_8$ are each independently a single bond, alkylene, or cycloalkylene, and Y is arylene, cycloalkylene, heteroarylene, arylene-arylene, or arylene-CR'R"-arylene, where R' and R" form a carbon ring group together with a carbon atom to which R' and R" are bonded), where the alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl; k is 0 or 1; X⁻ is a monovalent anion having an oxidation potential higher than a reduction potential of a dication of General Formula 1 by 3.1 V or greater; and $W^{2+}$ is the dication represented by General Formula 2,

[General Formula 2]

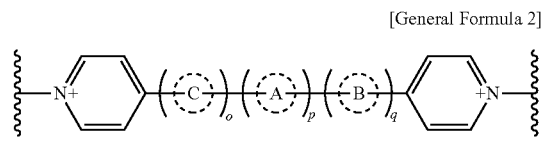

where, in General Formula 2, o, p, and q are each independently 0 or 1; and A, B, and C are each independently an arylene group that may have a substituent and has from 2 through 20 carbon atoms, or a heterocycle group.

<4> The electrochromic element according to <3>, wherein the electrolyte layer includes an electrolyte, and an anion of the electrolyte is a monovalent anion having an oxidation potential higher than a reduction potential of a dication of General Formula 1 by 3.1 V or greater.

<5> The electrochromic element according to any one of <1>, <2>, and <4>,
wherein the anion of the electrolyte of the electrolyte layer is one or more selected from the group consisting of $(FSO_2)_2N^-$, $(CF_3SO_2)_2N^-$, $(CB)_4B^-$, $BF_4^-$, $PF_6^-$, and $ClO_4^-$.

<6> The electrochromic element according to any one of <1> to <5>, wherein $R_1$ or $R_2$, or both $R_1$ and $R_2$ of General Formula 1 are a phosphonic acid group, a phosphoric acid group, a carboxylic acid group, a sulfonyl group, a silyl group, or a silanol group.

<7> The electrochromic element according to any one of <1> to <6>, Wherein one of $R_1$ and $R_2$ of General Formula 1 is a phosphonic acid group, a phosphoric acid group, a carboxylic acid group, a sulfonyl group, a silyl group, or a silanol group, and the other is a hydrogen atom, an aryl group having 14 or less carbon atoms, a heteroaryl group having 14 or less carbon atoms, a branched alkyl group having 10 or less carbon atoms, an alkenyl group having 10 or less carbon atoms, or a cycloalkyl group having or less carbon atoms.

<8> The electrochromic element according to any one of <1> to <7>, wherein X⁻ of General Formula 1 is one or more selected from the group consisting of $(FSO_2)_2N^-$, $(CF_3SO_2)_2N^-$, $(CN)_4B^-$, $BF_4^-$, $PF_6^-$, and $ClO_4^-$.

<9> The electrochromic element according to any one of <1> to <8>, wherein X⁻ of General Formula 1 is one or more selected from the group consisting of $(FSO_2)_2N^-$ and $(CF_3SO_2)_2N^-$.

<10> The electrochromic element according to any one of <1> to <9>, wherein X⁻ of General Formula 1 is $(CF_3SO_2)_2N^-$.

<11> The electrochromic element according to any one of <1> to <10>, wherein $W^{2+}$ of General Formula 1 is represented by Structural Formula 1,

[Structural Formula 1]

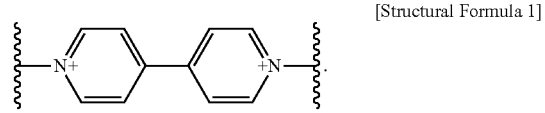 [SMILES: *[n+]1ccc(-c2cc[n+](*)cc2)cc1]

<12> The electrochromic element according to any one of <1> to <11>, wherein k of General Formula 1 is 0.
<13> The electrochromic element according to any one of <1> to <12>, wherein $R_3$ of General Formula 1 is represented by General Formula 3, and $R_4$ of General Formula 1 is represented by General Formula 4,

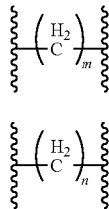

[General Formula 3]

[General Formula 4]

where m is 0 or an integer of from 1 through 10 in General Formula 3, n is 0 or an integer of from 1 through 10 in General Formula 4, and m and n may be identical values or different values.
<14> The electrochromic element according to any one of <1> to <13>, further including:
a second electrochromic layer disposed on or above the second electrode, wherein the electrolyte layer is disposed between the first electrochromic layer and the second electrochromic layer.
<15> The electrochromic element according to <14>, wherein the second electrochromic layer includes a polymer obtained by polymerizing a polymerizable material including a radical-polymerizable compound having a triarylamine skeleton.
<16> The electrochromic element according to <15>, wherein the polymerizable material further includes a radical-polymerizable compound having a tetraaryl benzidine skeleton.

The electrochromic element according to any one of <1> to <16> can solve the various problems existing in the art, and can achieve the object of the present disclosure.

What is claimed is:
1. An electrochromic element comprising:
a first electrode;
a second electrode disposed to face the first electrode with a gap between the first electrode and the second electrode;
a first electrochromic layer disposed on or above the first electrode, where the first electrochromic layer includes conductor or semiconductor nano-structures and an electrochromic compound;
a second electrochromic layer disposed on or above the second electrode, where the second electrochromic layer includes a mixture of triarylamine and tetraaryl-benzidine; and
an electrolyte layer including an electrolyte, disposed between the first electrochromic layer and the second electrode,
wherein the electrochromic compound is a compound represented by General Formula 1, and an anion of the electrolyte is a monovalent anion having an oxidation potential higher than a reduction potential of a dication of General Formula 1 by 3.1 V or greater,

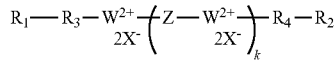

[General Formula 1]

where, in General Formula 1, $R_1$ and $R_2$ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, a phosphonic acid group, a phosphoric acid group, a carboxylic acid group, a sulfonyl group, a silyl group, or a silanol group; $R_3$ and $R_4$ are each an alkylene group having from 1 through 10 carbon atoms or an arylene group that may have a substituent and has 12 or less carbon atoms; Z is alkylene, cycloalkylene, or a divalent group represented by $—R_7—Y—R_8$, where $R_7$ and $R_8$ are each independently a single bond, alkylene, or cycloalkylene, and Y is arylene, cycloalkylene, heteroarylene, arylene-arylene, or arylene—CR'R''—arylene, where R' and R'' form a carbon ring group together with a carbon atom to which R' and R'' are bonded, where the alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl; k is 0 or 1; $X^-$ is a monovalent anion having an oxidation potential higher than a reduction potential of the dication of General Formula 1 by 3.1 V or greater; and $W^{2+}$ is the dication represented by General Formula 2,

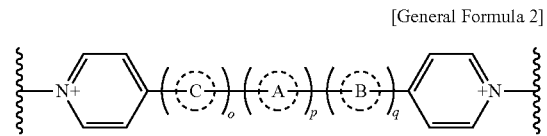

[General Formula 2]

where, in General Formula 2, o, p, and q are each independently 0 or 1; and A, B, and C are each independently an arylene group that may have a substituent and has from 2 through 20 carbon atoms, or a heterocycle group,
wherein the anion of the electrolyte of the electrolyte layer is one or more selected from the group consisting of $(FSO_2)_2N^-$, $(CF_3SO_2)_2N^-$, $(CN)_4B^-$, $BF_4^-$, $PF_6^-$, and $ClO_4^-$.

2. The electrochromic element according to claim 1, wherein the first electrochromic layer is a first electrochromic layer, in which the electrochromic compound is deposited on the nano-structures.

3. The electrochromic element according to claim 1, wherein $R_1$ or $R_2$, or both $R_1$ and $R_2$ of General Formula 1 are a phosphonic acid group, a phosphoric acid group, a carboxylic acid group, a sulfonyl group, a silyl group, or a silanol group.

4. The electrochromic element according to claim 1, wherein one of $R_1$ and $R_2$ of General Formula 1 is a phosphonic acid group, a phosphoric acid group, a carboxylic acid group, a sulfonyl group, a silyl group, or a silanol group, and the other is a hydrogen atom, an aryl group having 14 or less carbon atoms, a heteroaryl group having 14 or less carbon atoms, a branched alkyl group having 10 or less carbon atoms, an alkenyl group having 10 or less carbon atoms, or a cycloalkyl group having 10 or less carbon atoms.

5. The electrochromic element according to claim 1, wherein $X^-$ of General Formula 1 is one or more selected from the group consisting of $(FSO_2)_2N^-$, $(CF_3SO_2)_2N-$, $(CN)_4B-$, and $ClO_4-$.

6. The electrochromic element according to claim 1, wherein X⁻ of General Formula 1 is one or more selected from the group consisting of (FSO₂)₂N⁻ and (CF₃SO₂)₂N⁻.

7. The electrochromic element according to claim 1, wherein X⁻ of General Formula 1 is (CF₃SO₂)₂N⁻.

8. The electrochromic element according to claim 1, wherein W²⁺ of General Formula 1 is represented by Structural Formula 1,

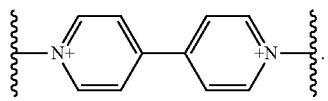

[Structural Formula 1]

9. The electrochromic element according to claim 1, wherein k of General Formula 1 is 0.

10. The electrochromic element according to claim 1, wherein R₃ of General Formula 1 is represented by General Formula 3, and R₄ of General Formula 1 is represented by General Formula 4,

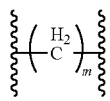

[General Formula 3]

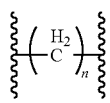

[General Formula 4]

where m is 0 or an integer of from 1 through 10 in General Formula 3, n is 0 or an integer of from 1 through 10 in General Formula 4, and m and n may be identical values or different values.

11. The electrochromic element according to claim 1, wherein the electrolyte layer is disposed between the first electrochromic layer and the second electrochromic layer, and the second electrochromic layer includes a polymer obtained by polymerizing a polymerizable material including a radical-polymerizable compound having a triarylamine skeleton, and the polymerizable material further includes a radical-polymerizable compound having a tetraaryl benzidine skeleton.

12. An electrochromic element comprising:

a first electrode;

a second electrode disposed to face the first electrode with a gap between the first electrode and the second electrode;

a first electrochromic layer disposed on or above the first electrode, where the first electrochromic layer includes conductor or semiconductor nano-structures and an electrochromic compound;

a second electrochromic layer disposed on or above the second electrode, where the second electrochromic layer includes triarylamine, or tetraarylbendizine, or a mixture of triarylamine and tetraarylbenzidine; and an electrolyte layer including an electrolyte, disposed between the first electrochromic layer and the second electrode, wherein the electrochromic compound is a compound represented by General Formula 1, and an anion of the electrolyte is a monovalent anion having an oxidation potential higher than a reduction potential of a dication of General Formula 1 by 3.1 V or greater,

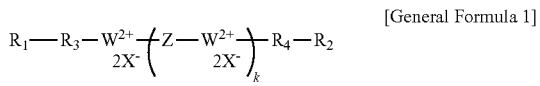

[General Formula 1]

where, in General Formula 1, R₁ and R₂ are each a hydrogen atom, an aryl group having 14 or less carbon atoms, a heteroaryl group having 14 or less carbon atoms, a branched alkyl group having 10 or less carbon atoms, an alkenyl group having 10 or less carbon atoms, a cycloalkyl group having 10 or less carbon atoms, a phosphonic acid group, a phosphoric acid group, a carboxylic acid group, a sulfonyl group, a silyl group, or a silanol group; R₃ and R₄ are each an alkylene group having from 1 through 10 carbon atoms or an arylene group that may have a substituent and has 12 or less carbon atoms; Z is alkylene, cycloalkylene, or a divalent group represented by —R₇—Y—R₈, where R₇ and R₈ are each independently a single bond, alkylene, or cycloalkylene, and Y is arylene, cycloalkylene, heteroarylene, arylene-arylene, or arylene—CR'R"—arylene, where R' and R" form a carbon ring group together with a carbon atom to which R' and R" are bonded, where the alkylene, the cycloalkylene, the arylene, the heteroarylene, and the carbon ring group may be substituted with one or more substituents selected from the group consisting of halogen, alkyl, alkoxy, alkyl thio, hydroxyalkyl, acyloxy, cycloalkyl, aryl, substituted aryl, aryloxy, heteroaryl, and substituted heteroaryl; k is 0 or 1; X⁻ is a monovalent anion having an oxidation potential higher than a reduction potential of the dication of General Formula 1 by 3.1 V or greater; and W²⁺ is the dication represented by General Formula 2,

[General Formula 2]

where, in General Formula 2, o, p, and q are each independently 0 or 1; and A, B, and C are each independently an arylene group that may have a substituent and has from 2 through 20 carbon atoms, or a heterocycle group, wherein the anion of the electrolyte of the electrolyte layer is one or more selected from the group consisting of (FSO₂)₂N⁻, (CF₃SO₂)₂N⁻, (CN)₄B⁻, BF₄⁻, PF₆⁻, and ClO₄⁻.

* * * * *